United States Patent
Hull, Jr. et al.

(10) Patent No.: US 11,253,496 B2
(45) Date of Patent: Feb. 22, 2022

(54) ALPHA KETO ACID COMPOSITIONS FOR TREATING HYPO-ALBUMINEMIA

(71) Applicant: Edgar L. Hull, Jr., Verona, WI (US)

(72) Inventors: Edgar L. Hull, Jr., Verona, WI (US); Rodell Barrientos, Greensboro, NC (US); Narashima Murthy, Bangalore (IN); Sridhara Am, Bangalore (IN)

(73) Assignee: Edgar L. Hull, Verona, WI (US)

( * ) Notice: Subject to any disclaimer, the term of this patent is extended or adjusted under 35 U.S.C. 154(b) by 77 days.

(21) Appl. No.: 16/768,230

(22) PCT Filed: Nov. 29, 2018

(86) PCT No.: PCT/US2018/063086
§ 371 (c)(1),
(2) Date: May 29, 2020

(87) PCT Pub. No.: WO2019/108809
PCT Pub. Date: Jun. 6, 2019

(65) Prior Publication Data
US 2020/0281881 A1    Sep. 10, 2020

Related U.S. Application Data

(60) Provisional application No. 62/772,590, filed on Nov. 28, 2018, provisional application No. 62/592,380, filed on Nov. 29, 2017.

(51) Int. Cl.
| | | |
|---|---|---|
| *A61K 31/198* | (2006.01) | |
| *A61K 31/192* | (2006.01) | |
| *A61K 31/405* | (2006.01) | |
| *A61K 31/4164* | (2006.01) | |
| *A61K 9/20* | (2006.01) | |
| *A61P 13/12* | (2006.01) | |
| *A61K 45/06* | (2006.01) | |

(52) U.S. Cl.
CPC .......... *A61K 31/198* (2013.01); *A61K 9/2027* (2013.01); *A61K 9/2054* (2013.01); *A61K 31/192* (2013.01); *A61K 31/405* (2013.01); *A61K 31/4164* (2013.01); *A61P 13/12* (2018.01); *A61K 9/2013* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,100,160 A * | 7/1978 | Walser | A61K 31/19 514/400 |
| 4,100,161 A | 7/1978 | Walser | |
| 4,100,293 A | 7/1978 | Walser | |
| 4,228,099 A | 10/1980 | Walser | |
| 4,352,814 A * | 10/1982 | Walser | A61K 31/195 514/400 |
| 4,677,121 A | 6/1987 | Walser et al. | |
| 4,752,619 A | 6/1988 | Walser et al. | |
| 4,957,983 A | 9/1990 | Hawrylko et al. | |
| 5,354,771 A | 10/1994 | Walser | |
| 2005/0100613 A1 | 5/2005 | Giordano | |
| 2005/0197397 A1 | 9/2005 | Martin | |
| 2009/0074883 A1 | 3/2009 | Gupta | |

FOREIGN PATENT DOCUMENTS

| | | |
|---|---|---|
| CN | 101416947 A | 4/2009 |
| CN | 102675079 A | 9/2012 |
| CN | 104187720 A | 12/2014 |
| EP | 0431465 B1 | 4/1994 |
| EP | 0747395 A1 | 12/1996 |
| WO | WO200226221 A2 | 4/2002 |
| WO | WO 2008122473 A2 * | 10/2008 |
| WO | WO2008122473 A2 | 10/2008 |

OTHER PUBLICATIONS

Thakkar et al. "Ultra Performance Liquid Chromatographic Method For Quantitative Analysis of Some Keto-Analogues of Essential Amino Acid Calcium Salt Used In Severe Rental Failure" 2013.*
EPO Search Report dated Feb. 15, 2021—"EESR 139939".

(Continued)

*Primary Examiner* — Danah Al-Awadi

(57) ABSTRACT

Provided herein are nutritional, or therapeutic, compositions and methods of use in primarily treating kidney patients suffering from low serum albumin. The compositions are divided into four formulations, comprising: 1) the magnesium salt and/or the calcium salt of the alpha keto acids of: α-leucine, α-valine, α-isoleucine, α-phenylalanine, α-hydroxy methionine; and/or α-tryptophan, and/or α-tyrosine; 2) L-lysine monoacetate, L-threonine; and/or 3) histidine, tryptophan, and tyrosine, as amino acids or base acids. The specific formulation administered depends in part upon which stage 2-5 of renal disease the patient has. The invention further comprises methods of treatment of disorders associated with low serum albumin using the composition as an over-the-counter pill. The patient's serum albumin is tested on a periodic basis and the selected composition and dose are adjusted accordingly. And the invention comprises method of making α-leucine, α-valine, α-isoleucine, a-tyrosine and α-tryptophan in a multi-step process.

8 Claims, 11 Drawing Sheets

(56) References Cited

OTHER PUBLICATIONS

India Search Report/Office Action dated Nov. 24, 2020—"PNP1204".

Jahnen-Dechent, W, and Ketteler, M., "Magnesium Basics", Clin. Kidney J. 2012: 5 (Suppl 1): i3-i14.

ZA Massy, TB Drueke, "Magnesium and outcomes in patients with chronic kidney disease: focus on vascular calcification, atherosclerosis and survival," Clin Kidney 5(Suppl 1): i52-61 (2012).

AP Silva et al., "Magnesium and Mortality in Patients with Diabetes and Early Chronic Kidney Disease," J Diabetes Metab, 5(3): 1-6 (2014).

W. Jahnen-Dechent et al., "Magnesium basics," Clin Kidney J. 5(Suppl 1): i3-i14 (2012).

PCT/US2018/063086, International Search Report/Demand, form 409, dated Mar. 19, 2020.

PCT/US2018/063086, International Search Report/Written Opinion, form PCT/ISA/220, dated Apr. 2, 2019.

\* cited by examiner

Prior Art: L-lysine monoacetate

Formula: $C_6H_{14}N_2O_2 \cdot C_2H_4O_2$
Molar Mass: 206.24 g/mol

Prior Art: Keto-analogue α-leucine (Calcium Salt)

Formula: $C_{12}H_{18}O_6Ca$
Molar Mass: 298.35 g/mol

Keto-analogue α-leucine (Magnesium salt)

Formula: $C_{12}H_{18}O_6Mg$
Molar Mass: 282.57 g/mol

Keto-analogue α-valine (Magnesium salt)

Formula: $C_{10}H_{14}O_6Mg$
Molar Mass: 254.52 g/mol

Prior Art: Keto-analogue α- phenylalanine (Calcium salt)

Formula: $C_{18}H_{14}O_6Ca$
Molar Mass: 366.78 g/mol

Ketoanalog α- phenylalanine (Magnesium salt)

Formula: $C_{18}H_{14}O_6Mg$
Molar Mass: 350.61 g/mol

Prior Art: Keto-analogue α-isoleucine (Calcium salt)

Formula: $C_{12}H_{18}O_6Ca$
Molar Mass: 298.35 g/mol

Keto-analogue α-isoleucine (Magnesium salt)

Formula: $C_{12}H_{18}O_6Mg$
Molar Mass: 282.57 g/mol

Prior Art: α- hydroxy methionine (Calcium salt)

Formula: $C_{10}H_{18}O_6S_2Ca$
Molar Mass: 338.46 g/mol

Keto Analogue of the α- hydroxy methionine (Magnesium salt)

Formula: $C_{10}H_{18}O_6S_2Ca$
Molar Mass: 338.46 g/mol

Prior Art: L-threonine (Neutral)

Formula: $C_4H_9NO_3$
Molar Mass: 119.12 g/mol

Prior Art: Histidine= β- Imidazolyl pyruvic acid

Formula: C6H6N2O3
Molar mass: 154.12 g/mol
CAS: 2504-83-8

Keto analogue α-histidine (Magnesium salt)

Formula: $C_{12}H_{10}N_4O_6Mg$
Molar Mass: 330.54 g/mol

Prior Art: L-Histidine

Formula: C6H9N3O2
Molecular Weight: 155.15
CAS Number: 71-00-1

Prior Art: Keto analogue α-Tyrosine

Free Acid without NH2 group
Formula: HOC6H4CH2COCO2H
Molecular Weight: 180.16
CAS Number: 156-39-8

Keto analogue α-tyrosine (Magnesium)

Formula: $C_{18}H_{14}O_8Mg$
Molar Mass: 382.60 g/mol

Prior Art: Keto Analogue α-Tryptophan

Formula: C11H9NO3
Molecular Weight: 203.19
CAS Number: 392-12-1

Keto analogue α-tryptophan (Magnesium salt)

Formula: $C_{22}H_{16}N_2O_6Mg$
Molar Mass: 428.68 g/mol

Routes of Synthesis    Mg salt of Keto analogue α-leucine

Routes of Synthesis    Mg salt of Keto analogue α-isoleucine

Routes of Synthesis: Mg salt of Keto analogue α-valine

Routes of Synthesis: Mg salt of Keto analogue α-tyrosine

ALPHA KETO ACID COMPOSITIONS FOR TREATING HYPO-ALBUMINEMIA

CROSS-REFERENCE TO RELATED APPLICATIONS

This application is a U.S. National Stage Application filed under 35 U.S.C. § 371 of International Application No. PCT/US18/63086 filed Nov. 29, 2018, which claims priority to provisional application 62/592,380 filed in the United States Patent Office on Nov. 29, 2017, and provisional application 62/772,590 filed in the United States Patent Office on Nov. 28, 2018. The entire disclosure of all listed patent applications are hereby enclosed by reference in their entirety.

FIELD OF THE DISCLOSURE

This disclosure generally relates to nutritional compositions for treating low serum albumin including low serum pre-albumin and particularly in patients with early stage (2, 3, 4) kidney and liver related disorders and diseases.

BACKGROUND OF THE DISCLOSURE

Chronic diseases, such as kidney disease, cause low serum albumin and low pre-albumin, a condition known as hypoalbuminemia, and/or protein malnutrition in patients. Serum albumin is one of the best and most accurate predictors of mortality in kidney disease and all patients. Pre-albumin is one of the best indicators of current or short term (e.g. a two to three day) protein malnutrition. Albumin is a long-term measure of protein malnutrition. We will use albumin to describe both albumin and pre-albumin in the disclosure. Safe long-term nutritional support is the goal, so albumin will be used in this disclosure.

Serum albumin levels lower than 4.6 g/dl increase mortality rates in many diseases, and serum albumin rates above 4.6 have normal mortality rates. Serum albumin levels below 2.5 g/dL have been associated with a risk of death 20 times greater as compared to the reference level of 4.0-4.6 g/dL in HD. Serum albumin levels of 3.5-3.9 g/dL were associated with double the risk of death.

There is currently no safe, specific and effective way to manage, improve or treat low serum albumin or protein malnutrition over the long term for the patient groups in the U.S. comprising, for example: kidney patients requiring low or very low protein diet to slow or stop the progression of kidney disease; kidney patients who do not choose a low protein or very low protein diet but who are not yet at end stage renal disease (ESRD) or on dialysis; kidney patients who are at end stage renal disease, on dialysis or on transplant list; all patients including preoperative and post-operative patients whose serum albumin is low and who may have illnesses or ailments that prevents normal protein metabolism; aging patients with age related decline in kidney function; and patients with Sarcopenia or age related muscle loss, protein energy wasting or liver disease patients and for patients who may have reduced kidney function due to disease or age.

A new way to manage serum albumin, protein malnutrition, calcium, magnesium and to safely slow disease progression earlier in stages two, three and four is described herein that does not increase mortality rates, health risks and does not contribute to, or cause an increase in, other comorbid conditions. Current approaches to treating protein malnutrition or low serum albumin increase the risk of heart disease/vascular calcification, high cholesterol, metabolic acidosis, inflammation, hypercalcemia, malnutrition, uremic toxemia, uremic malnutrition and edema.

The number one killer of kidney patients is heart disease caused by vascular calcification. Kidney disease is considered a perfect storm for accelerated heart disease. Low serum albumin contributes greatly to heart disease acceleration. Kidney disease treatment should incorporate treating heart disease specifically due to vascular calcification. What is needed is a new way to treat low serum albumin, hypo-albuminemia, that does not accelerate heart disease, which occurs at rates 200% to 500% greater in kidney patients than the healthy public. Slowing, stopping or possibly reversing heart disease and vascular calcification must be a part of any treatment for kidney disease patients.

Albumin is the major protein in the body making up 55% to 60% of total human plasma protein by mass. Many hormones and drugs are bound to albumin in the bloodstream and must be released before becoming active. Low albumin leads to an increase in serum calcium as calcium is unable to bind to normal albumin levels. This further contributes to heart disease via vascular calcification and hypercalcemia risk. Low serum albumin levels may also contribute to poor or abnormal drug delivery in the bloodstream.

Low serum albumin levels are a predictor of mortality in the following situations: Preoperative in all patients; Post-operative in all patients; Kidney disease; Pretreatment in cancer patients; Post treatment in cancer patients; Increased risk of heart failure in elderly adults; Heart disease; Ischemic stroke; all-cause mortality in long lived elderly; Transplant recipients; especially lung transplants; liver disease, Predictor of poor outcome in traumatic brain injury; Burn patients; Severe sepsis; Crohn's disease; and others. The cause for low serum albumin levels may be different I n each case, but raising serum albumin levels is beneficial in all cases of the listed situations.

Albumin levels can be raised by increasing intake of essential amino acids or branched chain amino acids. However, for many patients, traditional amino acids increase the workload on already taxed kidneys creating more health problems than they solve. Protein metabolism is severely impaired with patients eating a large amount of dietary protein to no effect. Increased dietary protein leads to an increase in factors that reduce serum albumin levels like acidosis, inflammation, uremia and others.

The term "alpha keto acid" refers to an alpha keto-carboxylic acid form, or "keto-analog" of an essential amino acid (EAA) (e.g., histidine, isoleucine, leucine, lysine, methionine, phenylalanine, threonine, tryptophan, and valine) or non-essential amino acid (non-EAA) (e.g., tyrosine) formed by the amine group being substituted by a ketone. Keto acids or keto amino acid blends have distinct advantages over traditional dietary protein consumption and traditional amino acid supplements. These benefits only apply to those patients with impaired amino acid or protein metabolism. In most cases, this impairment is related to handling protein metabolic products kidney, liver, aging, inflammation or microinflammation, metabolic acidosis, oxidative stress or related diseases.

Protein Metabolism Impairment in Kidney Disease Patients

Normal protein metabolism is impaired in kidney disease patients, which results in low serum albumin and/or chronic protein malnutrition in many patients. Kidney disease is a long-term chronic illness in most cases. The time from diagnosis to End Stage Renal Disease or dialysis can take from two to twenty-years depending on the disease and health of the patient. During these years, kidney patients suffer from low serum albumin or protein malnutrition for a variety of reasons, despite eating a normal to high-protein diet. As serum albumin levels fall, patients are susceptible to a variety of illnesses and fall prey to comorbid diseases like heart disease. As serum albumin levels fall, mortality rates rise dramatically.

In fact, heart disease is the number one cause of death for kidney patients. Long term kidney disease sets the stage for aggressive heart disease. Kidney patients are the highest risk group ever studied for heart disease. Specifically, vascular calcification is the leading cause of heart disease in kidney patients. A variety of reasons contribute to such high rates of heart disease in kidney patients. However, heart disease and vascular calcification start early in kidney disease as early as stage 2 kidney disease. Patients may go decades with low albumin levels. The prolonged chronic hypoalbuminemia contributes considerably to poor health, worse prognosis and higher mortality. In fact, low albumin accelerates many diseases including an increase in kidney disease progression and an increase in heart disease progression. Successfully managing albumin levels is imperative for patient health.

No treatment exists for patients with a Glomerular Filtration Rate (GFR) over 20 or in end stage renal disease. Previous formulations treated uremia for patients on dialysis or patients getting ready for dialysis. The recommendation is for GFR's to be below 20 or stage five kidney disease or treatment is contraindicated using past formulations for stage 2, 3 and 4 patients. Nutrition is formulated specifically for Stage 5 or end stage renal disease with a GFR below 20. This excludes all other patients with a GFR over 20 with different nutritional needs. No treatment exists to slow or stop the progression of kidney disease or raise serum albumin for patients with stage 2, 3 or 4 kidney disease or patients with a GFR greater than 20. The majority of patients are diagnosed at stage 3 with a GFR between 30 and 59. This group of patients has already started accumulating comorbid conditions and starting stages of heart disease. For this group, calcium-based solutions are not viable long-term treatment option and may be harmful over the long term. The time from stage 2 or 3 diagnosis to stage 5 is three to twenty years. For this reason, long term calcium based keto acids cannot be used. The longtime frame exposes the patients to more risk than benefit. A new formulation allows the opportunity to treat in early stages and to treat many drivers of kidney disease as inflammation, blood pressure, acidosis, uremia, uremic toxins etc., while increasing albumin levels early in the diagnosis.

Current formulations do not take dietary protein into account, thus resulting in higher levels of uremic toxins and uremia. The dosage must be adjusted by dietary protein intake to reduce the workload on already compromised kidneys. Current formulations recommend the same dosage regardless of protein intake. This is incorrect. A patient consuming 60 to 70 grams of protein per day dosage must be adjusted compared to the same patient consuming 20 to 30 grams a day. The result of not adjusting formulation dosage by adjusting dietary protein results in an increased protein workload with no benefits for some patients and others will be deficient in protein nutrition.

Current formulations do not allow patients and doctors to manage the amount or ratio of magnesium or calcium. Current formulations have only one option. Every patient is different with a range of conditions such as hyper/hypomagnesaemia and hypo/hypercalcemia being common. If Calcium based options are too high risk or results in new comorbid conditions, then patient must stop treatment with no other options. Patient is forced to choose between hypoalbuminemia or hypercalcemia. This is not optimal for the majority of patients. In reality, only a small percentage of patients will this actually work for. The unique nutritional needs of stage 2, 3, and 4 patients require unique formulations designed to maximize nutrition and minimize workload on the kidney and comorbid conditions. The nutritional needs of a stage 5 patient on dialysis are very different than an early stage 3 patient. The same formulations should not be used. Four formulations are needed to meet nutritional demands of different patient populations; and patients and doctors should be allowed to change formulations over time to improve nutritional status and to treat drivers of kidney disease progression. This allows patients and doctors to adjust dosage of magnesium and calcium while still providing protein nutrition. This is vital to long term treatment. As kidney disease progresses the needs of the patient will change from a higher magnesium tolerance to a lower magnesium tolerance. It is mandatory that options exist for this change as the disease progresses and still provide protein nutrition.

There has been no focus on treating and managing serum albumin, inflammation, oxidative stress and related factors over the long-term to increase survival of at-risk patients with low serum albumin over the long term. This requires a new approach to treat these conditions earlier before end stage renal disease occurs, or dialysis is required. Current therapies require patients to be in stage five kidney disease and or just prior to dialysis as evidenced by label claims. Aging combined with disease progression leads to a higher rate of hospitalization and increased number of comorbid conditions for these patients. Chronic and incurable diseases like Focal Segmental Glomerulosclerosis (FSGS) and other diseases may progress slowly over two to twenty-years. In these cases, low serum albumin levels may last decades. Low serum albumin levels over periods as short as 30 days may increase mortality rates.

During these long periods of dealing with a chronic illness, many patients will undergo surgeries, medical treatments, suffer injuries, transplants, dialysis, infections and suffer normal illnesses like colds and flu and emergency room treatments. Routine surgeries or medical procedures can become life-threatening with greatly increased morbidity and mortality rates if serum albumin levels are lower than 4.6 mg/dl. The lowest mortality rates have the highest serum albumin levels and the highest mortality rates have the lowest serum albumin levels.

Several reasons exist for low serum albumin. It is a multifactorial condition and disease and must be treated accordingly. These factors are as follows. (1) Proteinuria, which is the presence of large amounts of protein excreted in urine. Patients cannot achieve normal serum albumin levels or achieve protein nutrition through normal diet. (2) Inflammation, which reduces albumin concentration by decreasing its rate of synthesis. In extreme cases, increased transfer of albumin out of the vascular compartment occurs. (3) Metabolic Acidosis: low bicarbonate levels leading to acidosis are associated with low serum albumin levels, especially in stage 3 kidney disease. And (4) Oxidative stress, which is much higher in kidney patients. In fact, oxidative stress can be as much as 500% higher than in healthy patients. Proteins are oxidized at a much higher rate. The combination of these factors leads to a permanent and progressive impairment in the body's ability to digest and process dietary protein effectively. (5) Diet: the consumption of certain foods can greatly accelerate kidney disease. A low nitrogen diet or low protein diet may reduce nitrogen waste products at the expense of protein nutrition, wherein accelerated disease progression and muscle wasting can occur. In this situation, uremia is lessened, but at the expense of long-term health. Low protein diets without supplementation are not safe for any patients as albumin and Fetuin A levels decrease even further. High dietary protein diets are also not safe due the contributions to inflammation, oxidative stress, uremia and acidosis to name a few. The body operates in a narrow band of tolerances. This narrow range must be respected and dealt with accordingly. This narrow range is very difficult for kidney patients to maintain as kidney disease progresses. A special diet called the Kidney Factor Diet is part of the solution, so the stage is set for improved albumin levels, slowed disease progression and improved overall health. A safe long-term method is needed to treat and manage protein malnutrition and increase serum albumin levels to the normal ranges, but the solutions cannot create conditions that contribute to the acceleration of kidney or heart disease or any other comorbid conditions. The solution must set the stage for the body to produce normal albumin levels or to produce increased levels of albumin while not increasing other health risks, such as heart disease. A special diet and supplementation are needed to improve serum albumin levels as fast as possible.

Past combinations of amino acids or keto and amino acids have been targeted at treating only uremia at or near End Stage Renal Disease (Glomerular Filtration Rate-GFR of 20 or below) with very little remaining kidney function left. The goal is to delay the progression to dialysis up to a year by limiting uremic (protein) waste products, or to reduce the severity of uremia. However, dietary and supplemented treatment of uremia has not proven as effective as dialysis for end stage renal disease patients. Uremia by itself has not been proven to raise or lower albumin levels. For this reason, these formulations are questionable. Past combinations have been narrowly focused on treating one thing: uremia. They are single factor treatment plans. Single factor treatment plans will not work for multifactorial conditions. The other use has been to delay or slow the progression of kidney disease. The results are considered inconclusive and was not proven as a treatment. It was and at time of writing considered a failed drug trail (MDRD study 1989-1993). No keto amino acid treatment is available to U.S. patients at this time. When medical conditions like hypoalbuminemia are multifactorial in cause, treatment must be multifactorial as well. Single factor treatment plans have little chance of success.

DISADVANTAGES OF THE PRIOR ART

Past commercial formulations and methods of treatment have the following disadvantages.

Lack Long Term Safe Use

Current keto acid formulations are not meant for long term use. The use of keto acids as 100% calcium salts combined with amino acids have induced hypercalcemia in patients. Hypercalcemia and even calcium levels at the high end of the normal ranges accelerate cardiovascular disease/vascular calcification when combined with many diseases including kidney diseases and aging populations. This is also true for the general population. Heart disease and specifically vascular calcification is the number one killer of kidney patients. Vascular calcification occurs in kidney patients at a greatly accelerated rate compared to healthy adults. This is why existing formulations cannot be used over the long term or for patients with stage 2, 3 and 4 kidney disease. The risk of accelerated vascular calcification is too great. Daily calcium dosage exceeding the recommended daily allowance of 1,000 to 1,200 mg may strongly contribute to heart disease and vascular calcification and is not recommended for patients with impaired kidney function. Past commercial formulations subject patients to very high intake of calcium salts alone and/or when dietary calcium is taken into account. It has been proven that calcium supplements increase heart disease risk. Past formulation daily calcium dose ranges from 750 mg to 1,200 mg per day. The average American consumes 1,000 to 1,400 mg of calcium per day from dietary sources. This combination of diet and calcium salts results in daily calcium dose ranging from 1,750 to 2,600 mg per day, a dramatic increase over what is currently recommended. In order for patients to comply, they must take the recommended daily allowance limits of 1,000 to 1,200 mg per day. No dietary calcium can be consumed during the day. One cup of milk has 300 mg of calcium, one cup of cooked kale has 245 mg of calcium. It would be impossible for patients to stay below 1,200 mg per day if consumption through supplements is already averaging 1,000 to 1,200 mg. Dietary management of calcium is impossible if the supplement calcium load is this high to start with. To make matters worse, there is no option to control supplemental calcium intake and maintain protein nutrition; the patient must reject treatment or accept the risks of accelerated heart disease. There is currently no option that allows patients to manage supplemental calcium intake while still using keto acids as a treatment method. This daily large intake of calcium contributes to vascular calcification and heart disease in a very high-risk group even when calcium levels are in the normal range. Excess calcium leads to calcification when excess calcium is present. The most current research suggests a calcium limit of 1 gram per day and patients should not incur a positive calcium load. 800 mg for women and 1,000 mg for men is the total calcium load from all sources. Assuming a 50% split between dietary calcium and calcium from keto amino acids supplements, the patient cannot exceed 500 mg from each source. 500 mg from diet and 500 mg from the supplement. This fact leaves patients with nothing but bad choices that will increase mortality rates. Reduce keto and amino acid intake to 50% of the required dose leads to protein malnutrition. Another option is to try and reduce all calcium intake through dietary choices which is very hard as even fruit and vegetable are sources of calcium. Many foods today are fortified with additional calcium as well. Managing calcium is very tough for patients. Positive calcium load refers to any excess dietary calcium over what the body requires. Patients should consume the absolute minimum amount of calcium required to maintain normal to low normal range calcium levels and should not take calcium supplements without magnesium. The optimal calcium is one where the body's needs are met, but not one milligram more. Calcium should be in the low end of the normal range to reduce risks to an acceptable level for this high-risk group. A new method is needed to reduce the risk of vascular calcification, which may be the leading cause of death in kidney patients. This is especially true if the patients or the patient's family has a history of heart disease, obesity, lack of exercise, diabetes or high blood pressure. A method for supplying protein nutrition for a kidney patient that does not accelerate heart disease is desperately needed. Keto amino acid combinations are a single factor approach for treating low serum albumin. Keto acid supplements are currently produced as 100% calcium salts, but the resultant serum calcium concentration is extremely high. Therefore, free amino acids are often blended with keto acid calcium salts to control calcium intake. However, adding amino acids contributes to the nitrogen, acidosis and uremia. A new solution is needed.

Fetuin A

Blood albumin levels are related to Fetuin A. Fetuin A is the primary protein that inhibits vascular calcification and overall calcification of tissues. Fetuin A levels are correlated to serum albumin levels. Fetuin A is produced by the liver like albumin. Proper nutrition is required for production of albumin and Fetuin A. As albumin levels rise Fetuin A levels also rise. Fetuin A levels can be correlated with heart disease and vascular calcification. Increasing Fetuin A levels decreases the rate of vascular calcification. Low protein levels from impaired amino acid metabolism leads to chronic low levels of Fetuin A. Low protein diets are not safe for kidney patients unless supplemented with a safe alternative protein source as the formulations in this paper. Low Fetuin A was observed in low protein diets without supplementation. Low Fetuin A is not treated in kidney patients currently. By the time patients get to ESRD, heart disease and vascular calcification are present in most patients and thus heart disease is the number one killer of kidney patients. Patients have had low levels of the most active calcification inhibitor for decades leading to a vascular calcification accumulating each year until heart disease kills the patient.

The combination of reducing calcium intake while increasing Fetuin A levels (primary calcification inhibitor) is crucial to reducing the rate and risk of heart disease and vascular calcification in kidney patients. Reducing calcium and increasing Fetuin A while not placing a workload on the kidneys is the start of a synergistic multifactorial combination.

Inflammation

Inflammation is a primary driver of kidney disease progression, and inflammation increases as kidney disease progresses. Inflammation is one of the main causes of heart disease and may be a primary cause of low albumin levels when kidney disease is not present. The combination of increasing inflammation, low Fetuin A and high calcium from current methods could be a deadly combination for kidney patients. A method for providing protein nutrition that reduces inflammation is needed. Albumin acts as an anti-inflammatory and anti-oxidant but this effect is reduced when low albumin is present. Proteinuria or protein in urine is one of the reasons kidney patients have low serum albumin levels. Proteinuria is related to inflammation. The higher the inflammation markers, the more severe the proteinuria. Many food products and diets can cause increased inflammation and increased free radicals. Calcium based therapies do nothing to treat inflammation. Eating higher amounts of these products to increase protein intake can cause increased inflammation and increased proteinuria. Taking a protein supplement to treat low serum albumin without treating inflammation at the same time will not work in the majority of patients.

Magnesium

Levels of serum magnesium are inversely correlated with inflammation. Magnesium is inversely correlated with traditional market of inflammation like C Reactive Protein. The higher the magnesium levels, the lower the level of inflammation. Lowering inflammation may lower proteinuria and allow more protein to be utilized for maintenance and growth. Patients who go into remission or partial remission from kidney disease as measured by lower proteinuria have greatly extended life expectancies compared with patients who are not able to reduce inflammation and arrest the progression of kidney disease. The combination of lower calcium intake, higher Fetuin A and lower inflammation work together as a multifactor treatment to slow the progression of heart disease in kidney patients. Magnesium is correlated with albumin levels. Albumin is attached to magnesium in the blood stream. If magnesium levels are low, then albumin is normally low. Normal to high magnesium levels are needed to raise serum albumin.

Heart Disease/Vascular Calcification

Magnesium is proven to reduce vascular calcification and phosphate induced calcification in vascular muscle tissue. Phosphate induced calcification is the leading cause of vascular calcification in kidney patients. The combination of high calcium and high phosphorus accelerate heart disease/vascular calcification process. Increasing magnesium concentrations may significantly reduce vascular calcification. Higher magnesium levels are associated with lower mortality in kidney patients. A synergistic effect occurs when calcium and magnesium are combined. Calcium and magnesium compete for absorption this lowering intake of both. This factor may help decrease calcium intake even when calcium intake is higher than desired. The combination of: lower calcium intake, higher Fetuin A, lower inflammation, higher magnesium intake, work together to slow the progression of heart and kidney disease while providing protein nutrition. Again, a multifactorial treatment is needed.

High blood pressure: magnesium reduces blood pressure; but calcium does not. High blood pressure is a common driver of kidney and heart disease progression. Supplemental magnesium intake reduces blood pressure and allows patients to consume a lower amount of blood pressure medication, in most cases.

Magnesium intake is inversely correlated to Type 2 diabetes. Diabetes is one of the most common causes of kidney disease. Improving magnesium nutrition may reduce the severity of diabetes.

Arterial stiffness: magnesium reduces endothelial dysfunction as measure by arterial stiffness, and it reduces the risk of heart disease and stroke.

Nitrogen Loads

Nitrogen loads are also a risk factor for kidney and heart disease progression. "Nitrogen load" as defined herein is the amount of nitrogen that kidneys are forced to process on a daily basis. One of the primary functions of the kidney is to remove protein or nitrogen waste products from the bloodstream. These waste products are extremely toxic and lead to death if not removed by dialysis. Diseased or aging kidneys' ability to remove these wastes is impaired leading to uremia. Past formulations of nine essential amino acids result in over 1,500 mg of nitrogen load being placed on kidneys per serving each day without counting dietary protein intake. When dietary protein is added, the nitrogen load is very similar to traditional diets. Past combinations of keto and amino acids results in a 600 to 800 mgs of nitrogen. This reduction may be the reason that keto acids may slow the progression of kidney disease by 50% compared to amino acids. However, this reduction is not high enough for all patients to benefit. The nitrogen load needs to be as low as possible for kidneys that are struggling to clean waste products from the bloodstream so that waste products can be removed from the body even if kidney function is very low. Using a new approach nitrogen loads can be as low as 150 to 250 mg of nitrogen using the average daily dose depending on the formulation. Kidney's functioning at 20% of normal capacity or even lower benefit from a 70%+ reduction in workload. Extreme reductions in nitrogen and ammonia waste products are needed to improve patient's health due to kidney functioning 70% to 80% below the normal range. This represents a dramatic workload reduction for kidneys compared to ingesting dietary protein or traditional amino acid supplements or past keto amino acid blends. It is now possible to provide protein nutrition with a fraction of the previous nitrogen loads depending on the formulation This means increased protein nutrition with little to no additional workload on our kidneys. This is especially important as most patients do not wish to, or do not comply fully with low protein or very low protein diets. Dietary protein can be increased while the total nitrogen is still reduced using a lower nitrogen formulation. This may improve dietary compliance. Past solutions required patients to be on a low protein diet. Patient compliance is very low for stringent diets. These patients are already consuming more protein than desired, thus incurring a significant nitrogen load, yet still suffering from low albumin levels. Providing nutrition that does not create any nitrogen load, or the lowest possible nitrogen load, is crucial. Uremia is more manageable and uremic toxins levels drop when additional nitrogen loads are much lower. Uremia is also related to heart disease and vascular calcification progression and kidney disease progression. The combination of lower calcium intake, higher Fetuin A, higher albumin, lower inflammation and a reduction in cardio and nephrotoxic uremic toxins work together to slow the progression of heart disease in kidney patients. Thus, seven factors are being addressed by this approach as disclosed herein compared to single factor approaches used in the past. A multifactorial approach for a multifactorial condition.

The importance of reducing nitrogen intake cannot be over emphasized. The prior art discloses formulations comprising 5 amino acids and 5 keto acids, which increases nitrogen load and increases calcium intake, which are two things that should be avoided. The present invention reduces calcium intake; and it can eliminate calcium intake if needed and lower the nitrogen load by using a composition comprising two or three amino acids and seven to eight alpha keto acids as the primary treatment as opposed to prior art's five alpha keto acids and five amino acids.

Metabolic Acidosis

Past methods may produce or increase metabolic acidosis. Dietary protein consumption in an attempt to raise blood albumin levels can result in metabolic acidosis. The same is true for amino acid and keto amino acid blends. This is especially true for formulations with the amino acid methionine. Diseased or aging kidneys cannot produce enough ammonia to offset the higher acid diets and keep PH in the normal range. Past advice is for patients to consume high quality proteins like chicken, beef, fish and eggs. However, animal proteins strongly contribute to acidosis. Acidosis is also a contributor to kidney and heart disease progression. Reducing dietary protein and replacing it with keto acids or with certain keto amino acid blends lowers the acid load the kidneys have to offset by producing high PH ammonia. Amino acids contribute to acidosis, but keto acids do not. A growing amount of research shows that renal acid load may be one of the primary reasons for progressive kidney disease. Potential renal acid load or PRAL is a calculation used to determine the effect of dietary intake on kidneys. Negative PRAL's are desired, the more negative the more alkaline the food product. Negative PRAL's reduce or eliminate acidosis. Past formulations of amino acids have a PRAL of +8.2 to +9.5, which is considered highly acidic. These high PRAL levels show that amino acids contribute strongly to acidosis. Past formulations of keto acids and amino acids have a PRAL of −1.2 to +1.9. New formulations as disclosed herein using magnesium, or a combination of calcium and magnesium, with a PRAL between −7.4 and −8.9 depending on the formulation. These strongly negative PRAL numbers reduce or may eliminate acidosis, one of the primary drivers of low serum albumin. Past treatments of acidosis have involved sodium bicarbonate, which is effective, but increases salt intake in patients who are already on a salt restricted diet. Increased salt intake leads to high blood pressure, edema and reduced renal blood flow. A no salt treatment is needed for this population. Acidosis is also correlated to heart disease and kidney disease progression. A reduced methionine formulation combined a negative PRAL may control acidosis instead of contributing to acidosis like past formulations. The significance of a reduction in acid load shows up not only in kidney patients. Athletes experience an increase in ammonia production using dietary proteins. However, supplementation with keto amino acids significantly reduce recovery time and increase endurance. The reduction in ammonia allows muscles to recovery faster. The same is true for kidney patients. Reducing ammonia production reduces kidney workload on already impaired kidneys. A keto acid supplement benefits a professional or serious athlete by reducing their muscle recovery time. Kidney patients who are active and exercising also experience the benefit of decreased recovery time as well. This is important as kidney patients need to exercise to reduce heart disease risk factors.

Hyper Kidney Filtration

Past methods may induce hyper kidney filtration. Glomerular hyperfiltration contributes to localized high blood pressure in the kidneys. This is caused by human kidneys processing a high protein and high acid load. Hyperfiltration accelerates kidney disease progression. Pure keto acids greatly reduce hyperfiltration by reducing the need for the kidneys to increase blood pressure, which further damages the kidneys. Hyperfiltration and acid load are related as high acid foods trigger a hyperfiltration response.

Edema and Swelling

Increasing albumin levels reduces edema and swelling. Low albumin levels contribute to edema and swelling. Salt restriction and diuretics are typically used to reduce edema. However, increasing serum albumin levels increases oncotic pressure. Albumin comprises 75-80% of normal plasma colloid oncotic pressure. If albumin levels can be increased swelling will also decrease. Lower amounts of diuretic can be taken by patients reducing side effects and costs for patients. Edema and swelling can contribute to mortality rates in kidney disease patients.

Phosphorus levels—High phosphorus levels accelerate heart and kidney disease. Phosphate induced vascular calcification is the primary driver of accelerated heart disease. Phosphorus comes from many dietary sources. Inorganic phosphorus is also present in most prepared foods, but not a required disclosure on nutrition labels. Most if not all patients are consuming more phosphorus than expected. Limiting phosphorus is a common theme in kidney patient diets. If a diet is not enough to reduce phosphorus, then phosphate binders are used. The most common binders are calcium-based phosphorus binders. A patient could be on a calcium salt based keto amino acid blend and also be taking calcium-based phosphate binders. These binders can easily add 500 to 1500 mg of calcium each day. A combination of all sources can easily be over 2,500 to 3,000 mg per day. The progress of calcification can slow if phosphorous and calcium levels can be controlled. However, controlling phosphorus using calcium-based binders may still increase heart disease. Magnesium is an effective phosphorus binder and a combination of magnesium and calcium in a keto acid blend had the extra effect of binding phosphorus at the same time while not adding any dietary phosphorus. Binding phosphorus while reducing calcium intake and increasing magnesium intake is yet another factor in the multifactorial approach to treating kidney disease Drug delivery: Many drugs bind to albumin to provide delivery. When albumin levels are low, drug delivery can be impaired. Increasing albumin levels improves drug delivery and increases the odds that the drug will be delivered properly and reduce toxicity.

Dosage problems Past recommendations do not take into account patients reduced kidney function/stage of kidney disease, dietary protein intake or input from current albumin levels. Dosage instructions comprise taking 4 to 8 pills a day or taking 3 of servings per day regardless of current kidney function or dietary protein intake. This is inadequate and unlikely to lead to increased albumin except in the most mild cases of kidney disease or leads patients to taking very high doses without guidance. Dosage should be based on the absolute lowest workload for already struggling kidneys while providing protein nutrition. The two issues of adequate protein nutrition and lowest possible nitrogen and ammonia load on kidneys need to be balanced. Prior recommendations provide no adjustment based on dietary protein intake. For example, a patient with stage five kidney disease consuming 30 grams of dietary protein is very different from a stage three patient consuming 60 grams of dietary protein per day. A different formulation must be used; and a method for ensuring protein nutrition with the minimum workload in an already ailing kidneys is needed. Workload on kidneys can actually be increased by not adjusting protein supplement by dietary protein intake. This could increase blood urea nitrogen levels, uremia, acidosis etc.

Multifactor treatment: The combination of the known factors that contribute to low serum albumin and decreased health for kidney and all patients with low serum albumin are addressed by the present invention, such as: proteinuria, inflammation, oxidative stress, low magnesium, phosphorus reduction, no or little nitrogen load, uremia, acidosis, hyperfiltration, edema and heart disease due to vascular calcification. In addition, the risks of accelerated heart disease are reduced dramatically. None of these treatments will work in isolation. For example, raising Fetuin A may be ineffective if calcium intake is 1,500 to 2,000 mg a day. Acidosis may continue to accelerate heart and kidney disease even if protein nutrition needs are met by amino acids or amino keto acids blends. Kidney disease is a complicated and systemic disease. The solution must be systemic and multifactorial. Past treatments were one factor treatments and have not been proven effective for this reason.

Diet: A specialized diet is used along with the supplements disclosed herein. A diet high in anti-inflammatory, antioxidants, high fiber, high calorie, and low in: protein, saturated fats, sodium, potassium and phosphorus is a part of the treatment plan. This diet is called the "Kidney Factor" diet. Patients can look up a food item to see what the estimated workload is on the kidneys. Kidney Factor.

Rating scores for foods and meals are based on the major diet factors that affect kidney disease patients: calories, protein, fiber, magnesium, calcium, phosphorus, sodium, saturated fat, antioxidant value as measured by Oxygen Radical Absorbance Capacity (ORAC), methionine and polyphenol content. Foods are listed with percentage of recommended daily intake for kidney disease patients to demonstrate which foods put the lowest workload on kidneys with the highest benefit. This is called the Kidney Factor diet. For example, past low protein diets for uremia have focus on low protein only. These low protein foods and diets rely on oils/fats, artificial creamers, rice/potato/corn starches and special low protein foods to keep protein low and keep calories high. However, these foods have no antioxidants and increase inflammation. In addition, these foods are nutrient poor resulting in poor nutrition despite adequate calories. Again, lowering protein is only one part of the treatment plan. As inflammation subsides during treatment serum albumin will rise. A combination of lower inflammation, high antioxidant intake and keto amino acid blend all work synergistically to increase albumin levels. Kidney Factor is a tool for kidney patients to evaluate food choices using the following data: protein, calories, calcium, magnesium, phosphorus, sodium, potassium, serving size, Advanced Glycation Products (AGE's), methionine and antioxidant values. Over the counter or prescription anti-inflammatory supplements/drugs have not proven effective in increasing albumin levels. The reason is low serum albumin is a systemic issue, not a single factor. Treating uremia or inflammation in isolation like past approaches have little if any chance for success. The Kidney Factor diet speeds serum albumin increases by eliminating those foods that cause oxidative stress, inflammation, uremia and acidosis. All of these conditions are linked to hypoalbuminemia. Diet is an integrated part of the treatment plan and mandatory for rapid increase in albumin levels. Albumin levels may rise without the diet but will do so at a much slower pace.

Salts— Ca+Mg

Past formulas and methods do not address primary drivers of illness in kidney patents like hypercalcemia, early stage kidney disease (2, 3, 4) inflammation, heart disease/vascular calcification, acidosis and other conditions. Past options may actually increase risk for some patients instead of reducing risks over the long term.

100% Calcium salts increases the risk of heart disease and vascular calcification Sodium salts are not allowed when most patients are on a salt restricted diet and salt contributes to high blood pressure, the second largest cause of kidney disease. Sodium salts should only be used in when sodium is below 100 mg a day.

Aluminum salts have proven toxic.

Potassium salts cannot be used as most kidney patients are on a potassium restricted diet and have trouble keeping potassium levels low.

Zinc and iron salts cannot be used as the daily recommended daily allowance is so low.

Phosphate binding—Low phosphorus levels are key to kidney patient survival. Calcium is used as an oral phosphate binder. Calcium use is well known as a phosphorus binder. However, the combination of calcium and magnesium keto acids also acts as a phosphate binder reducing phosphate levels in patients. Reducing phosphate levels also reduces the rate of vascular calcification and heart disease. Phosphorus is also a mortality indicator in kidney patients. The combination of magnesium and calcium is as effective as 100% calcium treatments, but without the same risks. Magnesium nutrition is also maintained without exceeding the recommended daily amounts of calcium or magnesium.

In the past, it was not cost effective to produce keto acids of tyrosine and tryptophan. Tyrosine and Tryptophan contribute to uremic toxins p-cresol sulphate and indoxyl sulfate when used as amino acids. The keto acids contribute a lower amount to these toxins compared to the amino acid forms. A cost-effective way was needed to product tyrosine and tryptophan as magnesium salt.

Past formulations do not allow targeting of different stages of kidney disease or comorbid conditions. One formula applies to all. However, it is possible and desirable to target levels of protein nutrition, calcium, magnesium and nitrogen load. A formula for a stage three patient with a family history of heart disease should be very different than a stage 4 patient who has persistent hypocalcemia or hypomania's.

Nutrition and Safety

Keeping calcium and magnesium supplementation initially below the RDA limit provides sufficient nutrition while allowing patients to consume a more natural diet without the same risks. Taking between 0 and 650 mg of calcium from supplementations of keto acids allows for the user to consumer another 400 to 1,000 mg in their diet. Dietary calcium does not increase the risk of heart disease; but calcium supplements are responsible for the increased heart disease risk. Magnesium in the present invention is provided at 5% to 100% of the recommended RDA initially. Magnesium supplementation does not increase heart disease risk, it lowers heart disease risk. The difference is magnesium levels in the higher end of the normal range or slightly exceeding the normal range are correlated with lower mortality in kidney patients. This is the opposite of calcium. Kidney patients with magnesium at the high end of normal or slightly exceeded the normal range have better outcomes. Increasing magnesium consumption is very important for kidney patients.

The optimal ratio of calcium to magnesium has not been established for kidney patients and different stages of kidney disease. A tailored dosage is the only solution. Low serum albumin equates to impaired calcium management. Impaired kidney function leads to poor control of magnesium levels. One patient may need 100% magnesium keto acids due to chronic hypercalcemia and the presence of heart disease. Another patient may be struggling with hypermagnesemia and need low magnesium and higher calcium. To further complicate treatment, these needs will change as kidney disease progresses yet current therapies do not allow for any manipulation of calcium and magnesium intake as the disease progresses it becomes harder and harder for patients to control these levels. Different blends of magnesium and calcium keto acids can be tailored to each patient's needs. A ratio from 100% magnesium to 100% calcium in extreme cases can be used to help patients keep levels in the normal ranges. Patients, doctors and nutritionists can choose the correct amount of magnesium and calcium based on current blood tests. A one size fits all model cannot provide the correct nutrition as the disease progresses and a patient's needs change. The goal will always be the maximum amount of magnesium and the lowest amount of calcium a patient can safely tolerate. Different formulations are needed to allow patients to better control these levels. Patients in poor health and impaired kidney function cannot be expected to successfully manage these issues without help. The supplement, as disclosed in the present inventions, must do the work and management for the patient. The optimal ratio will be different for different patients. Getting this ratio correct is an integral part of the supplementation. A custom blend is possible based on specific patient needs.

Muscle Strength

Proper nutrition must be provided for the special needs of kidney patients. Despite a normal intake of dietary protein, the branched chain amino acids, valine, leucine and isoleucine are lower in kidney patients. These essential amino acids are crucial for maintaining and building muscle. This is necessary for patients who experience protein energy wasting (PEW) and or sarcopenia associated with aging. The increase in mortality/morbidity rates for kidney patients due to muscle loss is exhibited by grip strength and other chronic conditions. Decreasing grip strength is a mortality indicator caused by protein malnutrition and lack of exercise in kidney patients. Strength decreases due to poor nutrition and low levels of muscle building valine, leucine and isoleucine. Past formulations do not increase keto or amino acids of value, leucine and isoleucine. Dr. William Rose's research was pioneering at the time, 1955. Today, sixty-two years later, we know much more about amino acid metabolism and requirements. Current formulations are based on data that is over sixty years old when it comes to the recommended daily amounts. Increased amount of the keto acids of valine, leucine and isoleucine are needed compared to past formulations. Increasing amounts of valine, leucine and isoleucine compensate for increased loss and oxidation of amino acids in kidney patients.

Alpha Keto Amino Acids

The compositions of the present invention are far superior to past compositions, which induce a variety of problems, including: edema, increase in cholesterol or dietary cholesterol; increase in blood pressure; increase in uremia; increase in inflammation; increase in liver workload; production of uremic toxins; increase in sodium and saturated fat intake; unsafe dosages; decreased bowel movements which decreases excretion of uremic toxins; and increase in symptoms of uremia.

Dosing: the prior art also discloses an incomplete method of determining the amount of amino acid supplement to administer to a patient. Dosage in the past simply comprised taking one serving of amino acid supplement three times a day (e.g. a dose of 94 mg a day of essential amino acids per kg of the patent's weight) or a wide range like "take 4 to 8 tablets per meal" This dose does not take into account other essential factors, such as: dietary intake of protein and current albumin levels, current magnesium and calcium levels. In order to be successful at increasing albumin levels while dramatically reducing workload on the kidneys, several factors must be accounted for in the treatment plan. The method of calculation must take into account current serum albumin levels. If starting a new treatment, albumin may not be known, so new patients need a method of calculating dosage to achieve the lowest possible workload on kidneys. The present invention resolves these short comings by disclosing a novel method of computing the proper dose of amino acids for patients that is based on the patient's amino acid metabolism impairment, and not only on their body weight.

SUMMARY

Novel Compounds and Compositions

Described herein are novel formulations of amino acids and alpha (α) keto acids that overcomes the disadvantages of prior art formulations. These novel formulations produce the lowest nitrogen load possible while providing a necessary nitrogen balance. This reduces the workload on the body to the lowest possible levels which is required to increase GFR numbers. The formulations described herein produce no metabolic acidosis. The formulations herein produce no hypercalcemia, no hyperphosphatemia, little if any kidney hyper filtration and have a negative potential renal acid load to reduce acidosis. The formulations described herein reduce edema and raise serum albumin levels. The formulations described herein produce no or very little uremic toxins. The formulations do not increase uremia, blood pressure, cholesterol, or inflammation. The dosages of the ingredients in the formulations are at safe levels that occur naturally in the body. All ingredients are provided at levels lower than any recommended daily allowances. The formulations may increase bowel movement which leads to an increased excretion of uremic toxins.

The formulations are specific to each patient's ability to metabolize magnesium, calcium, and alpha-keto or amino acids. Formulations range from 100% magnesium salts to a 80% to 100% calcium salts can be used. The ability to change the dosage of magnesium and calcium is a very important part of the treatment plan and supplement. The goal is for the patient to receive the proper amount of protein nutrition and take the highest tolerable dose of magnesium. Magnesium reduces inflammation, which in turn could reduce proteinuria and related albumin losses. Providing the highest tolerable dosage of magnesium and the lowest nitrogen workload are two key components. The formulations change over time for each patient as the patient's ability to metabolize magnesium, calcium and keto/amino acids change. For some patient's, their disease progression will be slowed but continue. These patients may need increasing doses of the formulation disclosed herein. Other patient's disease will slow or stop progressing, and thus they will be able to reduce or eliminate supplementation in the future. The ratio of calcium to magnesium is an important and novel part of the treatment and supplement-formulation. Many variations of the calcium salts, magnesium salts and amino acids can be produced; however, which specific keto acid is a calcium salt or magnesium salt is not as important as the ratio of calcium to magnesium. The ratio of calcium to magnesium is one of the most important parts of the formulations and treatment plan. This ratio can be tailored to specific treatment goals and management of specific conditions. This has not been possible before. The ratio of calcium to magnesium focuses on reducing inflammation and slowing heart disease progression while providing protein nutrition. The ratio of calcium to magnesium can be custom made to specific patient needs. Current technology allows for desktop or small run pill production. The exact formulation can be tailored to patient's current kidney function, albumin, serum calcium and serum magnesium levels. Standards formulations will never be optimal for most patients. Doctors and patients need to the ability to address specific conditions as needed to slow the progression of kidney and heart disease and or increase serum albumin.

Provided herein are nutritional, or therapeutic, compositions and methods of use in primarily treating kidney patients suffering from low serum albumin. The compositions are divided into four formulations, comprising: 1) the magnesium salt and/or the calcium salt of the alpha keto acids of: α-leucine, α-valine, α-isoleucine, α-phenylalanine, α-hydroxy methionine; and/or α-tryptophan and/or α-tyrosine; 2) L-lysine monoacetate, L-threonine; and/or 3) histidine, The specific formulation administered depends in part upon which stage 2-5 of renal disease the patient has. The invention further comprises methods of treatment of disorders associated with low serum albumin using the composition as an over-the-counter pill. The patient's serum albumin is tested on a periodic basis and the selected composition and dose are adjusted accordingly. And the invention comprises method of making α-leucine, α-valine, α-isoleucine, and α-tyrosine and α-tryptophan in a multistep process.

Novel chemical compounds of the present disclosure comprise seven magnesium salts of alpha keto acids of six EAA's and one non-EAA.

The novel chemical structures of the present invention comprise: 1) the magnesium salt of the keto analog of α-leucine (FIG. 3); 2) the magnesium salt of the keto analog of α-valine (FIG. 4); 3) the magnesium salt of the keto analog of α-phenylalanine (FIG. 6); 4) the magnesium salt of the keto analog of α-isoleucine (FIG. 8); 5) the magnesium salt of α-hydroxy methionine (FIG. 9B); 6) the magnesium salt of the keto analog of α-histidine (FIG. 11B); 7) the magnesium salt of the keto analog of α-tyrosine (FIG. 12B); and 8) the magnesium salt of the keto analog of α-tryptophan (FIG. 13B).

In an embodiment, the present invention comprises a nutritional or therapeutic composition, comprising for a keto analogue of an amino acid at least one of, or any combination thereof: 1) a magnesium salt; or 2) a calcium salt; or 3) a calcium salt and a magnesium salt; 4) wherein the keto analogue of the amino acid comprises: I) a α-leucine; ii) a α-valine; iii) a α-isoleucine; iv) a α-phenylalanine; v) a α-methionine; vi) L-lysine monoacetate; vii) L-threonine.

A composition comprising the S2 formula for treating stage 2 kidney disease may further comprise: histidine as an amino acid or keto analog; and tryptophan as a keto acid magnesium salt, or a base acid. Furthermore, the leucine, valine, isoleucine, phenylalanine, and methionine are as keto acid magnesium salts.

A composition comprising the S3 formula for treating stage 3 kidney disease may further comprise: histidine as an amino acid; and tryptophan keto acid as magnesium salt. Furthermore, the leucine, valine, isoleucine are as keto acid magnesium salts; and phenylalanine and methionine as keto acid/analogue calcium salts.

A composition comprising the S4 formula for treating stage 4 kidney disease may further comprise: histidine as an amino acid; tyrosine as an amino acid, or a base acid magnesium salt; and tryptophan as a keto acid magnesium salt. Furthermore, the leucine, valine, and isoleucine are present as both a keto acid calcium salt and a magnesium salt; while phenylalanine and hydroxy methionine as present as keto acid calcium salts.

A composition comprising the S5 formula for treating stage 5 kidney disease may further comprise: histidine as an amino acid; tyrosine as an amino acid, or a base acid magnesium salt; and tryptophan as a keto acid magnesium salt. Furthermore, the leucine, valine, isoleucine phenylalanine and hydroxy methionine as present as keto acid calcium salts.

In an embodiment, the nutritional or therapeutic composition further comprising a free histidine amino acid, or a magnesium salt, or a calcium salt, or a calcium salt and a magnesium salt, of a keto analogue of a α-histidine.

In an embodiment, the nutritional or therapeutic composition further comprises a free tyrosine amino acid, or a magnesium salt, or a calcium salt, or a calcium salt and a magnesium salt, of a keto analogue of a α-tyrosine.

In an embodiment, the nutritional or therapeutic composition further comprises a magnesium salt, or a calcium salt, or a calcium salt and a magnesium salt, of a keto analogue of a α-tryptophan.

In an embodiment, the nutritional or therapeutic composition further comprises a α-hydroxy methionine, or a magnesium salt, or a calcium salt, or a calcium salt and a magnesium salt, of a keto analogue of a α-hydroxy methionine.

In an embodiment, the nutritional or therapeutic composition further comprises L-lysine monoacetate, and/or L-threonine.

In an embodiment, the nutritional or therapeutic composition is formulated as a tablet with an excipient comprising one of more of: microcrystalline cellulose, povidone K-30, crospovidone, magnesium stearate, and Instacoat aqueous.

In the embodiments disclosed in Tables 1-4, the composition comprises the active ingredients of: about 8 to 31% wt/wt of the alpha keto analogue of leucine; about 5 to 21% wt/wt of the alpha keto analogue of valine; about 3 to 16% wt/wt of the alpha keto analogue of isoleucine; about 6 to 10% wt/wt of the alpha keto analogue of phenylalanine; about 3 to 5% wt/wt of the alpha keto analogue of hydroxymethionine; about 9 to 13% wt/wt of L-lysine monoacetate; about 5 to 8% wt/wt of L-threonine; and/or about 0 to 0.7% wt/wt of tyrosine or the Mg or salt of the alpha keto analogue of tyrosine; and about 0 to 0.4% wt/wt of tryptophan, or the alpha keto analogue of tryptophan; and/or about 2 to 4v % wt/wt of histidine amino acid or a calcium or magnesium salt of the α keto analog of histidine.

In an embodiment, the nutritional or therapeutic compositions disclosed herein comprise a nitrogen load that does not exceed 3.8%.

In an embodiment, the nutritional or therapeutic compositions disclosed herein comprise a calcium load that does not exceed 6.5%.

In an embodiment, the nutritional or therapeutic compositions disclosed herein comprise a magnesium load that is at a minimum level of 2.2%.

In an embodiment, the nutritional or therapeutic compositions disclosed herein comprise a sodium load that does not exceed 0.8%.

Methods of Treatment—Conditions, Diseases, and Formulations

The compositions disclosed herein are used for the prevention (prophylactic), or treatment and management of hypo-albuminemia (i.e. low serum albumin), and/or to maintain/promote a healthy nutritional status to increase survival rates for these patient groups, as well as for other groups requiring boosts to serum albumin (e.g. athletes to improve post workout recovery times). The present invention further comprises a method for supplying protein nutrition that does not accelerate heart disease. The present invention further comprises a method for supplying protein nutrition that does not accelerate heart disease.

In an embodiment, the method of treatment comprises administering one of the compositions of Tables 1-4, comprising the active ingredients of: the magnesium salt, or the calcium salt, or both salts of the alpha keto acid of leucine, valine, isoleucine, phenylalanine, hydroxy-methionine, tyrosine and tryptophan; and the free amino acids: histidine, L-threonine; and L-lysine monoacetate. In an alternative embodiment, the composition further comprises the magnesium salt of α-histidine in lieu of the free amino acid histidine.

In an embodiment, the composition comprises orally administering one of the low nitrogen compositions disclosed herein, such as in a tablet form, after determining the proper dose.

In an embodiment, the present invention comprises a method of treating a human patient having low serum albumin comprising the steps of: 1) determining a baseline dose of a composition based on a patient's body weight, and a current protein intake for a low protein diet; 2) administering the composition for about 90 days; 3) conducting a serum albumin test on the patient at about 90 days, wherein: a) when the albumin level is above 4.0 g/dl, then maintain administration of the baseline dose; or b) when the albumin level is below 4.0 g/dl, then computing a second dose; and 4) wherein the composition comprises a keto analogue of an amino acid at least one of, or any combination thereof, of Tables 1-4 and/or the Appendices.

Method of Making

The present invention further comprises methods of manufacturing the magnesium salts of alpha keto acids from the calcium salt of the same alpha keto acid.

The present invention further comprises a method of making a magnesium salt of an alpha keto acid of the amino acid comprising valine, leucine, and/or isoleucine: 1) combining ingredients to make a composition comprising: a calcium salt of an amino acid valine, leucine, or isoleucine; a water; a hydrochloric acid; a methyl tert-butyl ether; and a magnesium carbonate; 2) stirring the composition for about thirty minutes; 3) allowing the composition to settle into two layers, and collecting the top organic layer, and adding water and magnesium carbonate to the top organic layer; 4) heating the composition for about one hour to about 60-65 degrees Celsius; 5) removing the solvent, cooling, and adding methyl-tert-butyl ether to the composition; 6) stirring the composition for about one hour at about 25-30 degrees Celsius; 7) filtering, washing, drying under vacuum, and storing the composition as a powder; and 8) wherein the powder is a consumable low nitrogen product orally administered within a food, a beverage, or a tablet or pill.

The present invention further comprises a method of making a magnesium salt of an alpha keto acid of tryptophan, comprising a three-stage sequential process per Appendix A: producing a first compound comprising a 5[4-hydroxyphenyl) methylidene] imidazolidine-2,4-dione (TYM-I) in stage 1; producing a second compound comprising a 3-(4-hydroxyphenyl)-2-oxopropanoic acid (TYM-II) in stage 2 from the first compound; and producing a third compound comprising a magnesium salt of the alpha keto acid of a tyrosine in stage 3 from the second compound. In an embodiment, first compound is produced by combining P-hydroxy benzaldehyde, hydantoin, piperidine, process water, and hydrochloric acid. In an embodiment, second compound is produced by combining to the first compound: p-hydroxy benzyl hydantoin; process water; sodium hydroxide; hydrochloric acid; ethyl acetate; and hexane. In an embodiment, the third compound is produced by combing to the second compound: methanol; process water; magnesium carbonate; and methyl tertiary-butyl ether (MTBE).

The compositions and their method of use, together with additional objects and advantages thereof, will be best understood from the following description of specific embodiments when read in connection with the accompanying drawings, and examples—e.g. appendixes.

DETAILED DESCRIPTION OF EXEMPLARY EMBODIMENTS

Glossary of Terms

As used herein, the term "load", refers to the amount in grams or milligrams or grams/deciliters (g/dL) of nitrogen, calcium, sodium, and magnesium in the composition.

As used herein, the term "optimal dosage" refers to as the smallest amount of amount of the composition to raise and then maintain serum albumin to normal levels of 4.6 or higher.

As used herein, the term "about" refers to +/− five percent of the stated number or value.

As used herein, the term "alpha keto acid" refers to the alpha (α) ketocarboxylic acid, which is the "ketoanalog" or "keto analogue" of an amino acid formed from the amino acid being substituted by a keto group. Keto acids or ketoacids are organic compounds that contain a carboxylic acid group and a ketone group—see FIGS. 1-17. It is also noted that "keto analogue of α-leucine, α-valine, α-isoleucine, α-phenylalanine, α-methionine, α-tryptophan" and so forth is equivalent to the alpha keto acid of leucine, valine, isoleucine, phenylalanine, tryptophan, and so forth.

Magnesium Salts of Keto Acids:

Described herein are compositions that are novel magnesium salts of alpha keto acids, including the magnesium salt of the keto analog of α-histidine, the magnesium salt of the keto analog of α-tyrosine, the magnesium salt of the keto analog of α-valine, the magnesium salt of the keto analog of α-tryptophan, the magnesium salt of the keto analog of α-leucine, the magnesium salt of the keto analog of α-isoleucine, the magnesium salt of the keto analog of α-hydroxy methionine, and the magnesium salt of the keto analog of α-phenylalanine. (These compounds are known in the prior art only as calcium and sodium salts).

Novel Keto Acid—Magnesium Salt Compounds

Figure 1:
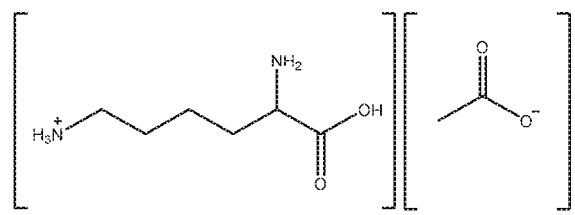
FIG. 1 illustrates the prior art chemical structure and formula for L-lysine monoacetate.
Figure 2:
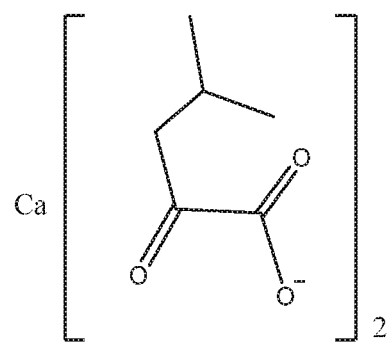
FIG. 2 illustrates the prior art chemical structure and formula for keto-analogue α-leucine (calcium salt).
Figure 3:
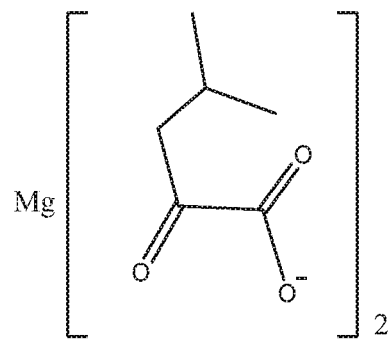
FIG. 3 illustrates the chemical structure and formula for the keto-analogue of α-leucine (magnesium salt).
Figure 4:
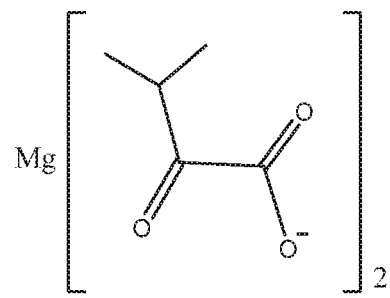
FIG. 4 illustrates the chemical structure and formula for the keto-analogue of α-valine (magnesium salt).
Figure 5:
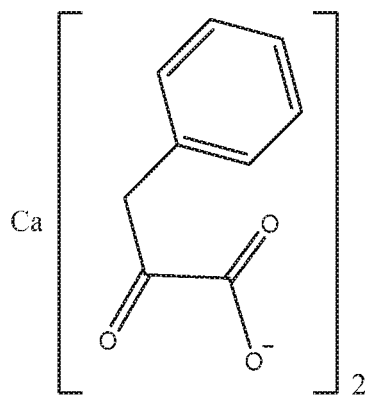
FIG. 5 illustrates the prior art chemical structure and formula for the keto-analogue of α-phenylalanine (calcium salt).
Figure 6:
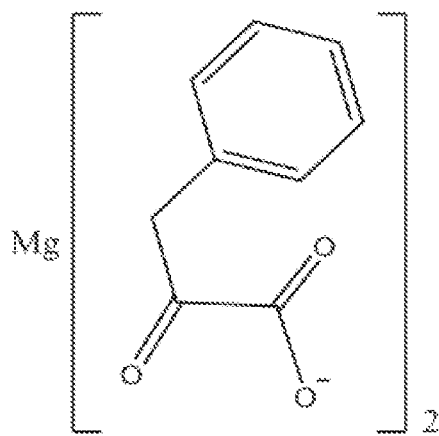
FIG. 6 illustrates the chemical structure and formula for the keto-analogue of α-phenylalanine (magnesium salt).
Figure 7:
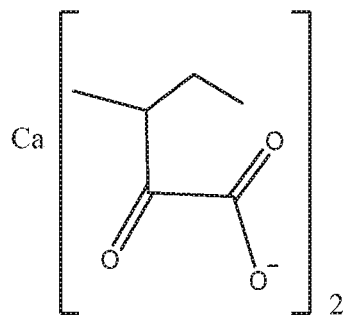
FIG. 7 illustrates the prior art chemical structure and formula for the keto-analogue of α-isoleucine (calcium salt).
Figure 8:
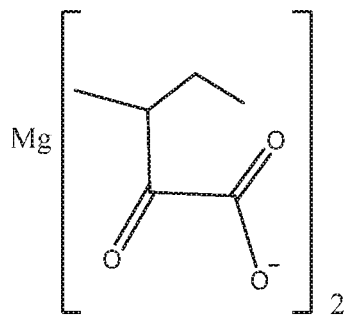
FIG. 8 illustrates the chemical structure and formula for the keto-analogue of α-isoleucine (magnesium salt).
Figure 9A:
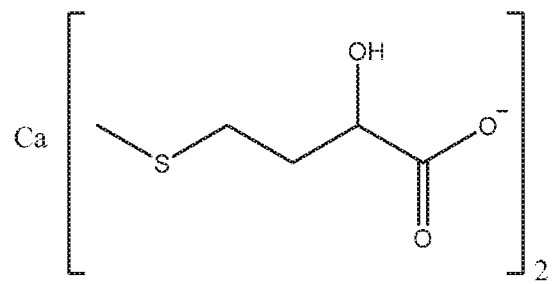
FIG. 9A illustrates the prior art chemical structure and formula for α-hydroxy methionine (calcium salt).
Figure 9B:
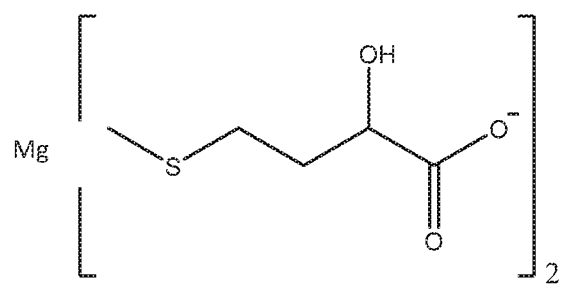
FIG. 9B illustrates the chemical structure and formula for α-hydroxy methionine (magnesium salt).
Figure 10:
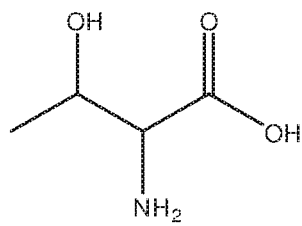
FIG. 10 illustrates the prior art chemical structure and formula for L-threonine (neutral).
Figure 11A:
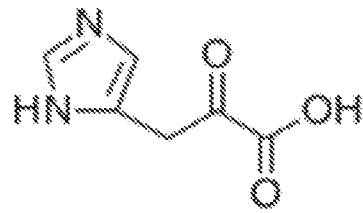
FIG. 11A illustrates the prior art chemical structure and formula for the keto-analogue of α-histidine.
Figure 11B:
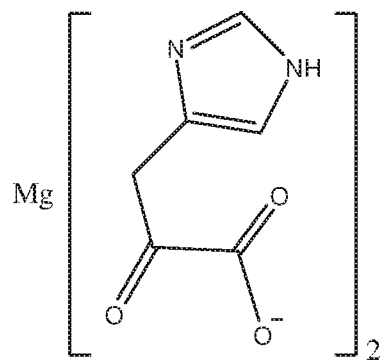
FIG. 11B illustrates the chemical structure and formula for the keto-analogue of α-histidine (magnesium salt).
Figure 11C:
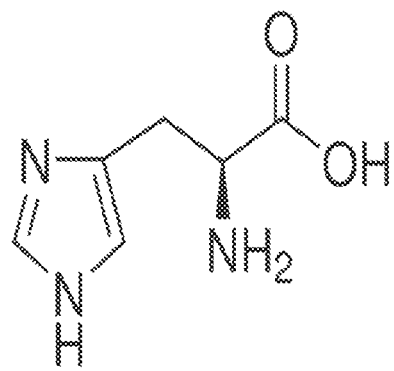
FIG. 11C illustrates the prior art chemical structure and formula for L-histidine.
Figure 13A:
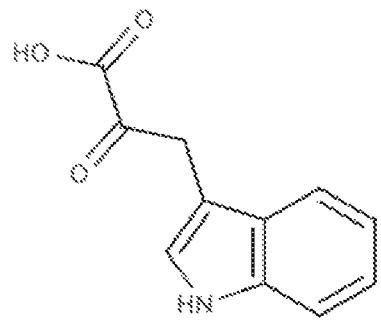
FIG. 13A illustrates the prior art chemical structure and formula for α-tryptophan.
Figure 13B:
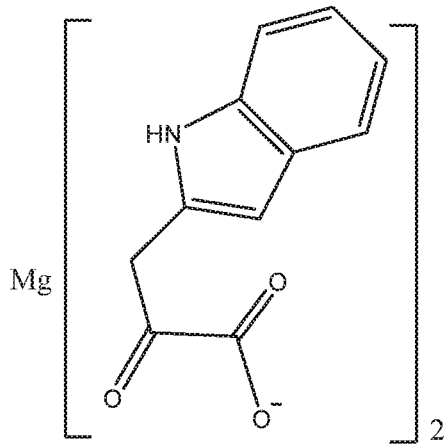
FIG. 13B illustrates the chemical structure and formula for one embodiment of the keto-analogue of α-tryptophan (magnesium salt).
Figure 14:
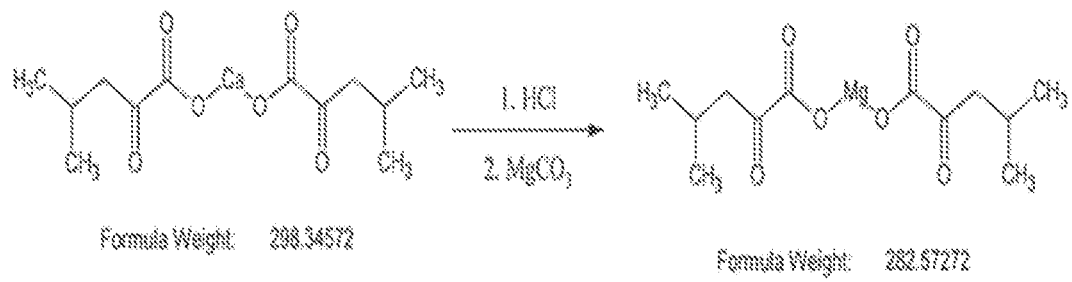
FIG. 14 illustrates the chemical reactions for the manufacturing process of the magnesium salt of the alpha keto acid of leucine.
Figure 15:
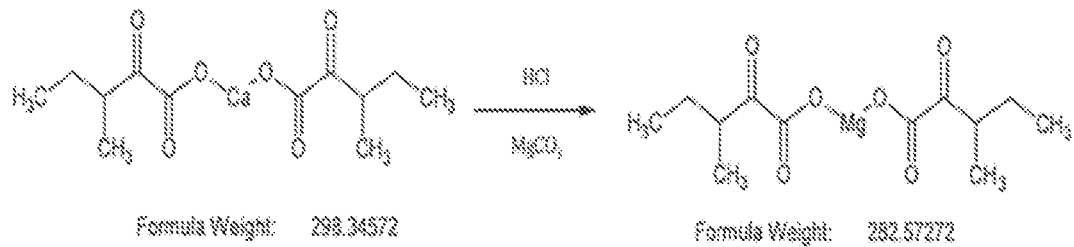
FIG. 15 illustrates the chemical reactions for the manufacturing process of the magnesium salt of the alpha keto acid of isoleucine.

The present disclosure further comprises novel alpha (α) keto acids of EAA and/or non-EAA compounds, formulas, compositions comprising, compositions consisting essentially of, and/or compositions consisting at least one of the novel magnesium salts listed supra (#1-9), which are derived by reacting the amino acid with magnesium oxide or magnesium hydroxide—see figures disclosing their molecular formula, molar mass, and chemical structure, comprising:

1) the magnesium salt of the keto analog of α-leucine (FIG. 3);

2) the magnesium salt of the keto analog of α-valine (FIG. 4);

3) the magnesium salt of the keto analog of α-phenylalanine (FIG. 6);

4) the magnesium salt of the keto analog of α-isoleucine (FIG. 8);

5) the magnesium salt of the α-hydroxy methionine (FIG. 9B);

6) the magnesium salt of the keto analog of α-histidine (FIG. 11B);

7) the magnesium salt of the keto analog of α-tyrosine (FIG. 12B); and/or 8) the magnesium salt of the keto analog of α-tryptophan (FIG. 13B).

Formulations Comprising Magnesium Salts:

Several reasons exist for using magnesium salts instead of calcium salts. A pure calcium salt formula like current or past formulations can cause hypercalcemia in patients. Another group of patients may not meet the criteria for hypercalcemia but have calcium levels in or near the highest normal range. High calcium levels accelerate heart disease in kidney patients. Calcification of arteries is accelerated by high calcium levels. Calcification is also accelerated by calcium supplementation. Magnesium is used to stop this from occurring. Magnesium ameliorates and may prevent future phosphate induced calcification in vascular smooth muscle. Not only does adding magnesium reduce calcium content, it also reduces the effect of calcium. Low magnesium is a mortality indicator for kidney and heart patients. Magnesium nutrition is provided by the formulation. Previous formulas contain no magnesium. Magnesium is rarely a problem in kidney patients and is not restricted in most cases. By reducing calcium, patients get 0% to 65% of the RDA with the average dose. Patients can get over 80% to 160% of the RDA of calcium with the older formulas. The old approach assumes dietary sources of calcium do not exist and that high calcium is not an issue. By consuming less than 65% of the daily RDA's, dietary intake is accounted for. This increases safety for long term use.

Formulations are described in herein that comprise at least one keto acid as a magnesium salt. In one embodiment, formulations comprise at least two alpha keto acids as their magnesium salts. In another embodiment, a formulation comprises at least three keto acids as their magnesium salts. In another embodiment, a formulation comprises at least four keto acids as their magnesium salts. In another embodiment, a formulation is described that comprises between one and eight keto acids as their magnesium salts.

In one embodiment, a formulation is described herein that comprises at least one magnesium salt of a keto acid, wherein the keto acid is selected from the group comprising histidine or the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

In another embodiment, a formulation is described herein that comprises at least two magnesium salts of keto acids, wherein the keto acids are selected from the group comprising histidine or the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

In another embodiment, a formulation is described herein that comprises at least three magnesium salts of keto acids, wherein the keto acids are selected from the group comprising histidine or the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenyl alanine.

In another embodiment, a formulation is described herein that comprises at least four magnesium salts of keto acids, wherein the keto acids are selected from the group comprising histidine or the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

In another embodiment, a formulation is described herein that comprises at least five magnesium salts of keto acids, wherein the keto acids are selected from the group comprising the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

In another embodiment, a formulation is described herein that comprises at least six magnesium salts of keto acids, wherein the keto acids are selected from the group comprising the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

In another embodiment, a formulation is described herein that comprises at least seven magnesium salts of keto acids, wherein the keto acids are selected from the group comprising the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

In another embodiment, a formulation is described herein that comprises at least eight magnesium salts of keto acids, wherein the keto acids are selected from the group comprising the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

Tables 1-4 comprise four exemplary formulations, claimed herein, that are used to correctly supply protein nutrition, increase albumin levels and manage magnesium and calcium levels for each stage of kidney disease and current patient health while reducing the risk of vascular calcification/heart disease. The formulations used allow exact dosing and management of these conditions during different phases or stages of kidney disease progression.

ALBUTRIX S2™ comprises a formula (composition) comprising 100% magnesium salts and three amino acids, no supplemental calcium or calcium salts for patients with persistent hypercalcemia or who can tolerate magnesium doses greater than the recommended daily amount of 400 mg. The targeted patient here is early stage kidney disease patient or stage 2 with a history or family history of heart disease.

ALBUTRIX S3™ comprises a formula comprising magnesium and calcium salts that provide the recommended daily amount of magnesium and minimal calcium. The target patient is a stage three patient.

ALBUTRIX S4™ comprises a formula comprising magnesium and calcium salts in which calcium and magnesium amounts are appreciably equal, and target patients who are in a stage four kidney patient.

ALBUTRIX S5™ comprises a formula comprising very low magnesium and higher calcium salts levels for stage five or end stage renal disease patients who already have magnesium levels above the normal range.

In the embodiments disclosed in Tables 1-4, the composition comprises the active ingredients of: about 8 to 31% wt/wt of the alpha keto analogue of leucine; about 5 to 21% wt/wt of the alpha keto analogue of valine; about 3 to 16% wt/wt of the alpha keto analogue of isoleucine; about 6 to 10% wt/wt of the alpha keto analogue of phenylalanine; about 3 to 5 wt/wt of the alpha keto analogue of methionine or hydroxy-methionine; about 9 to 13% wt/wt of L-lysine monoacetate; about 5 to 8% wt/wt of L-threonine; about 0 to 0.7% wt/wt of tyrosine or the Mg or salt of the alpha keto analogue of tyrosine; and about 0 to 0.4% wt/wt of tryptophan, or the alpha keto analogue of tryptophan without nitrogen; and/or about 2 to 4% wt/wt of histidine a.a., or a calcium or magnesium salt of the α keto analog of histidine.

In an exemplary embodiment, Table 1 discloses a composition in tablet form comprising magnesium salts of six alpha keto analogues, and three amino acids, and L-lysine monoacetate.

TABLE 1

| ALBUTRIX S2 ™ | | | |
|---|---|---|---|
| Active Ingredients | Mg/ Tablet | % wt/wt Active Ingredients | % wt/wt All Ingredients |
| Mg salt α keto analog of leucine | 236 | 30.37 | 24.97 |
| Mg salt α keto analog of valine | 156 | 20.08 | 16.50 |
| Mg salt α keto analog of isoleucine | 120 | 15.44 | 12.70 |
| Mg salt α keto analog of phenylalanine | 60 | 7.72 | 6.35 |
| Mg salt α keto analog of hydroxy methionine | 30 | 3.86 | 3.17 |
|  | 0 | 0 | 0 |
| Mg salt α keto analog Tryptophan; or base acid | 2 | .257 | .212 |
| Histidine amino acid., or Ca or Mg salt, or non-salt α keto analog of histidine | 30 | 3.86 | 3.17 |
| L-lysine monoacetate | 90 | 11.58 | 9.52 |
| L-threonine | 48 | 6.18 | 5.08 |

TABLE 1-continued

ALBUTRIX S2 ™

| Active Ingredients | Mg/Tablet | % wt/wt Active Ingredients | % wt/wt All Ingredients |
|---|---|---|---|
| Inactive Ingredients | | | |
| Microcrystalline cellulose | 101.01 | | 10.69 |
| Povidone (K30) ™ | 20.20 | | 2.14 |
| Crospovidone ™ | 20.20 | | 2.14 |
| Magnesium Stearate | 6.73 | | .712 |
| Instacoat Aqueous film coating-Readymix ™ | 20.20 | | 2.14 |

Combination of Magnesium and Calcium Salts

Tables 2 and 3 comprise compositions with a combination of magnesium and calcium salts of alpha keto analogues. The combination of magnesium and calcium reduces the possibility of exceeding RDAs. The combination of magnesium and calcium may be more effective, or as effective as, a phosphate binder than calcium salts alone. The combination is a safer way to reduce phosphorus than calcium alone.

TABLE 2

ALBUTRIX S3 ™

| Active Ingredients | Mg/Tablet | % wt/wt Active Ingredients | % wt/wt All Ingredients |
|---|---|---|---|
| Mg salt α keto analog of leucine | 226 | 29.08 | 23.92 |
| Mg salt α keto analog of valine | 151 | 19.43 | 19.43 |
| Mg salt α keto analog of isoleucine | 123 | 15.83 | 15.83 |
| Ca salt α keto analog of phenylalanine | 77 | 9.91 | 9.91 |
| Ca salt α keto analog of methionine | 36 | 4.63 | 4.63 |
| Mg salt α keto analog/keto acid tryptophan | 2 | .257 | .257 |
| Histidine amino acid | 25 | 3.22 | 3.22 |
| L-lysine monoacetate | 90 | 11.58 | 11.58 |
| L-threonine | 47 | 6.05 | 6.05 |
| Inactive Ingredients | | | |
| Microcrystalline cellulose | 101.01 | | 10.68 |
| Povidone (K30) ™ | 20.20 | | 2.6 |
| Crospovidone ™ | 20.20 | | 2.6 |
| Magnesium Stearate | 6.73 | | .867 |
| Instacoat Aqueous | 20.20 | | 2.6 |

TABLE 3

ALBUTRIX S4 ™

| Active Ingredients | Mg/Tablet | % wt/wt Active Ingredients | % wt/wt All Ingredients |
|---|---|---|---|
| Ca salt α keto analog of leucine | 71 | 9.14 | 7.51 |
| Ca salt α keto analog of valine | 47 | 6.05 | 4.97 |
| Ca salt α keto analog of isoleucine | 38 | 4.89 | 4.02 |
| Ca salt α keto analog of phenylalanine | 55 | 7.08 | 5.82 |
| Ca salt α keto analog of hydroxy methionine | 28 | 3.60 | 2.96 |
| Mg salt α keto analog of leucine | 160 | 20.59 | 16.93 |
| Mg salt α keto analog of valine | 115 | 14.80 | 12.17 |
| Mg salt α keto analog of isoleucine | 76 | 9.78 | 8.04 |
| Mg salt α keto analog tryptophan | 2 | .257 | .217 |
| Histidine amino acid | 30 | 3.86 | 3.17 |
| L-lysine monoacetate | 95 | 12.22 | 10.05 |
| L-threonine | 56 | 7.21 | 5.93 |
| Mg salt α keto analog of tyrosine; free or base acid Mg salt | 4 | .515 | .423 |

TABLE 3-continued

ALBUTRIX S4 ™

| Active Ingredients | Mg/Tablet | % wt/wt Active Ingredients | % wt/wt All Ingredients |
|---|---|---|---|
| Inactive Ingredients | | | |
| Microcrystalline cellulose | 101.01 | | 10.69 |
| Povidone (K-30) | 20.20 | | 2.14 |
| Crospovidone | 20.20 | | 2.14 |
| Magnesium Stearate | 6.73 | | .713 |
| Instacoat Aqueous | 20.20 | | 2.14 |

TABLE 4

ALBUTRIX S5 ™

| Active Ingredients | Mg/Tablet | % wt/wt Active Ingredients | % wt/wt All Ingredients |
|---|---|---|---|
| CA salt α keto analog of leucine | 236 | 30.37 | 24.97 |
| CA salt α keto analog of valine | 156 | 20.08 | 16.50 |
| CA salt α keto analog of isoleucine | 120 | 15.44 | 12.70 |
| CA salt α keto analog of phenylalanine | 60 | 7.72 | 6.35 |
| CA salt α keto analog of methionine | 30 | 3.86 | 3.18 |
| Mg salt α keto analog tryptophan | 2 | .257 | |
| Histidine amino acid | 30 | 3.86 | 3.18 |
| L-lysine monoacetate | 90 | 11.58 | 9.52 |
| L-threonine | 48 | 6.18 | 5.08 |
| Mg salt α keto analog of tyrosine; free or base acid Mg salt | 5 | .643 | .529 |
| Inactive Ingredients | | | |
| Microcrystalline cellulose | 101.01 | | 10.69 |
| Povidone (K-30) | 20.20 | | 2.14 |
| Crospovidone | 20.20 | | 2.14 |
| Magnesium Stearate | 6.73 | | .713 |
| Instacoat Aqueous | 20.20 | | 2.14 |

In one or more embodiments, the alpha keto acid of the non-EAA is: the keto analogue of alpha-tyrosine.

And in one or more embodiments, the alpha keto acid of the EAA is: α-histidine, α-tyrosine, α-valine, α-tryptophan, α-leucine, α-isoleucine and α-phenylalanine.

And the compositions may further comprise one or more of the following as a neutral compound, or as a calcium salt, or as a novel magnesium salt: L-lysine monoacetate, L-threonine, and/or α-hydroxy methionine.

The histidine is a free amino acid, or it is a magnesium and/or a calcium salt of an alpha (α) keto acid, or a neutral amino acid (e.g. FIGS. 11A, 11B, and/or 11C).

In one embodiment, a formulation comprises at least one magnesium salt; and/or a calcium salt and a magnesium salt of a keto acid, wherein the keto acid is selected from the group comprising the of: the keto analog of α-histidine, the keto analog of α-tyrosine, the keto analog of α-valine, the keto analog of α-tryptophan, the keto analog of α-leucine, the keto analog of α-isoleucine, the keto analog of α-hydroxy methionine, and the keto analog of α-phenylalanine.

Table 5 discloses other non-magnesium and non-calcium formulations of the EAA's and tyrosine that may be used within the compositions disclosed herein.

TABLE 5 of Free Acid (No Salt) EAA's and Tyrosine

Figure 12A:
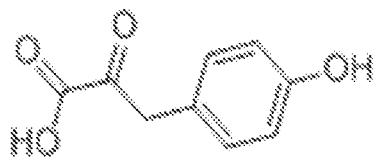
FIG. 12A illustrates the prior art chemical structure and formula for keto-analogue of α-tyrosine as a free acid without an NH2 group.
Figure 12B:
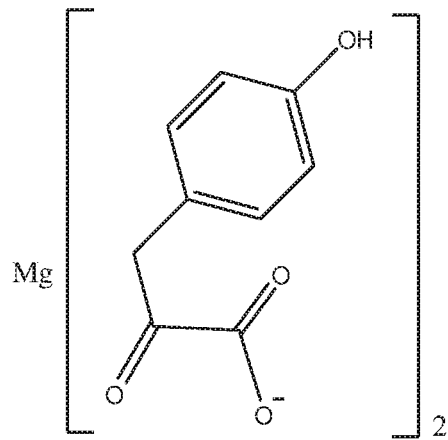
FIG. 12B illustrates the chemical structure and formula for the keto-analogue of α-tyrosine (magnesium salt).

| Amino Acids | Keto Form (no Mg or Ca salt) | Keto-form (CAS#) | FIG. # |
|---|---|---|---|
| Lysine | N/A | N/A | |
| Leucine | α-Ketoisocaproic acid | 816-66-0 | |
| Valine | α-Ketoisovaleric acid | 759-05-7 | |
| Phenylalanine | β-Phenylpyruvic acid | 156-06-9 | |
| Isoleucine | α-Keto-β-methylvaleric acid | 39748-49-7 | |
| Methionine | 2-keto-4-methylthiobutyric acid | 583-92-6 | |
| Threonine | N/A | N/A | |
| Histidine | β-Imidazolyl pyruvic acid | CAS: 2504-83-8 | FIG. 11A |
| | L-Histidine | CAS: 71-00-1 | or 11C |
| Tyrosine | 4-Hydroxyphenylpyruvic acid | 156-39-8 | FIG. 12A |
| Tryptophan | β-Indolepyruvic acid | 392-12-1 | FIG. 13A |

Nitrogen Load

Compositions in the Appendix comprise reduced nitrogen loads as measured by the total nitrogen content (mg) per average daily dose of the formulation. In one embodiment, a formulation is described herein that comprises amino acids and keto acids with a nitrogen load that does not exceed 10%. In one embodiment, the nitrogen load does not exceed 7.5%. In one embodiment, the nitrogen load does not exceed 5%. In a preferred embodiment, the nitrogen load does not exceed 3.8%.

Keto Acid: Amino Acid Content

Prior art formulations have used a combination of five amino acids and five keto acids. One or more formulations described herein contain higher amounts of keto acids to amino acids as compared to the prior art, such as: two amino acids; and seven alpha keto acids of essential amino acids (6) and non-essential amino acids (1). This allows nitrogen content to be reduced. Nitrogen wastes incur a workload on the kidneys. Reducing nitrogen waste products allows patients with compromised kidneys to receive sufficient protein without increasing kidney workload. This formulation has the lowest nitrogen load of any formulation.

Formulations comprising compositions in the Appendix comprise a mixture of amino acids and keto acids. In one embodiment, a formulation described herein comprises more keto acids than amino acids. In one embodiment, a formulation described herein comprises between 3 and 15 keto acids. In one embodiment, a formulation described herein comprises a maximum of 5 amino acids. In one embodiment, a formulation is described herein that comprise a maximum of 4 amino acids. In one embodiment, a formulation described herein comprises a maximum of 3 amino acids. In one embodiment, a formulation described herein comprises a maximum of 2 amino acids. In one embodiment, a formulation described herein comprises a maximum of 1 amino acid.

In some embodiments, the ratio of keto acid:amino acid is equal to or greater than 2:1. In one embodiment, the ratio of keto acid:amino acid is equal to or greater than 3:1. In another embodiment, the ratio of keto acid:amino acid is equal to or greater than 4:1. In one embodiment, the ratio of keto acid:amino acid is equal to or greater than 5:1.

Methionine Content

Methionine content has been too high in past formulations. Methionine is the most toxic of essential amino acids. Methionine contributes to acidosis which in turn accelerates kidney and heart disease. In 2007, the World Health Organization (WHO) reduced the daily recommended daily allowance for methionine. Methionine toxicity can also cause heart problems at high levels. Methionine metabolism may be impaired in kidney patients, so methionine is reduced to diminish risk of acidosis while still providing protein nutrition. The formulations in compositions of the Appendix comprise significantly less methionine than older formulations. Supplemental methionine is reduced to 270 mg in an average dose of nine pills. The recommended daily amount is 800 to 950 mg. However, real intake of dietary methionine is estimated at 125 to 507 mg/kg per day, which well in excess of actual needs. For this reason, methionine is reduced to compensate for dietary methionine intake.

Keto Acid Form of Tryptophan

In the formulations in the compositions the present disclosure, the keto acid form of tryptophan is used instead of the amino acid as in past formulas. Tryptophan is related to the production of uremic toxins like indoxyl sulfate. This risk is reduced in three ways. No tryptophan is used, or the keto acid of tryptophan and a reduced amount of tryptophan is used. The keto acid of tryptophan reduces production of indoxyl sulfate. Tryptophan dosage is supplemented at 27 to 30 mg per day at an average dose.

Keto Acid Form of Leucine

One of the issues affecting kidney patients is protein energy wasting and or muscle wasting. The amino acid leucine is related to muscle protein synthesis. A higher amount of the keto acid of leucine is used in the compositions disclosed herein to promote muscle synthesis and reduce protein energy wasting with no increase in nitrogen load This is also a benefit to aging or elderly patients.

Keto acid for of valine is one of the branched chain amino acids and supplied at a high dose to promote muscle synthesis and to compensate for reduced amino acid metabolism that is common in kidney patients Keto acid of iso-leucine is also one of the branched chain amino acids and is supplied at a higher does to promote muscle synthesis and to compensate for reduced amino acid metabolism that is common in kidney patients.

EXEMPLIFICATIONS: Formulations with limitations on nitrogen load, calcium load, and sodium load, methionine content as well as the minimum magnesium content.

In an embodiment, some of the compositions disclosed herein comprise amino acids and keto acids wherein at least one of the acids is present as a magnesium salt; or, as a magnesium and a calcium salt.

And/or the total elemental composition of calcium does not exceed 6.5%. And/or the total elemental composition of magnesium is a minimum of 2.2%. And/or the total elemental composition of sodium does not exceed 0.8%. And/or the nitrogen load may not exceed 3.8%.

Furthermore, the formulation may comprise: a magnesium salt of the keto analog of α-histidine as a magnesium salt; and/or a magnesium salt of the keto analog of α-tyrosine; and/or a magnesium salt of the keto analog of α-valine.

Therapeutic and Nutritional Goals

Treatment doses comprise the highest magnesium and the lowest calcium intake combined with the correct dosage of keto amino acid supplement based on severity of hypoalbuminemia. The treatment plan is based on three-month increment evaluations. As long as the patient is progressing, and serum levels are improving the diet continues. After a three-month evaluation with no improvement, a different set of decisions must be made. Patients are also encouraged to work on improving or curing comorbid conditions during each three-month period.

The first part is determining the correct dosage of keto/amino acids. The second is determining the correct amount of magnesium or calcium/magnesium blend that is appropriate for patient's current health and serum magnesium and calcium. Patient's with impaired kidney function cannot manage calcium and magnesium metabolism compared with a healthily adult. The work is done for the kidneys by selecting the appropriate formulation from 100% magnesium to a to a 90% to 100% of calcium to magnesium. The supplement helps the patients keep these numbers in check without the risks of hypercalcemia, hypocalcemia, hypermagnesemia and hypomagnesemia. Risk are significantly diminished, but protein nutrition is still provided.

Treatment plan takes place over a three-month period with monthly blood test. At the end of the three-month period, the highest magnesium formula that can be safely tolerated by the patient will be known. This dosage should be sustainable, well tolerated, safe and reduce inflammation and heart disease progression while providing the appropriate protein nutrition.

As the diet and supplement treatment progresses over time albumin levels will rise. The end goal is a daily maintenance dose of 100% magnesium salts as keto acids. Ideally, kidney patients will not consume supplemental calcium only dietary calcium. Depending on the severity of the hypoalbuminemia, the recommended dosage may contain more magnesium that can be safely tolerated. Calcium magnesium blends are used initially to determine the dosage the patient can tolerate. Different patients will respond differently depending on other illnesses or health conditions, current stage of kidney disease and compliance with Kidney Factor diet.

To raise serum albumin, inflammation and oxidative stress must be addressed. This diet ends up being a low protein diet Amino and keto acids are used to provide nutrition during the diet. The supplement and diet go hand and hand One can rarely be successful without the other. Both are required to raise albumin levels.

The first part of the diet has the goal of stopping kidney disease and or going into remission. This will not be possible for all patients. It is unknown now why some patients respond to the diet and supplement and others do not respond or respond more slowing. This diet is very strict in terms of foods allowed. The second part of the diet is a maintenance diet to keep kidney disease progression slowed and to increase nutrition. The maintenance diet may be relaxed after it is determined if the patient has the potential to slow disease progression. The reason is the combination of a protein source of keto acids does not contribute to inflammation, oxidative stress, acidosis and other conditions that contribute to lower serum albumin. This is true for all patients. Treating low serum albumin without treating inflammation and oxidative stress is unlikely to work alone.

The cycle for the diet is based on three-month increments. It will normally take up to four months on the diet and supplement for measurable changes to occur for patients with proteinuria. For this reason, the results are not evaluated until after 90 days on the diet and supplement. It takes this long for our bodies to start reducing oxidative stress or inflammation. At the end of three months, the effectiveness of the diet and supplement should be evaluated.

TABLE 6

Successful treatment with diet and supplement will have the following characteristics:

Increased serum albumin levels
Improved Creatinine clearance
Improved Blood Urea Nitrogen
Decreased inflammation measured as C reactive protein TABLE 6-continued Successful treatment with diet and supplement will have the following characteristics:

Serum magnesium at the high end of the normal range
Serum Calcium with in the normal range.
Reduced proteinuria
GFR near past GFR levels or slightly improved GFR

*A standard accepted test for oxidative stress does not exist. Oxidative stress is not measured.

If results are positive, continue with the diet for another three months. Repeat testing. If blood levels are increasing, continue the three-month cycle. At some point, patient's numbers will level out and continued treatment will not yield additional gains. The time frame for this is twelve to twenty-four months. Most patients can continue to see gains for twelve to fifteen months. The most severe patients may still be improving after 20 months.

One three-month period of stable results and evaluation should be made to determine is kidney disease has significantly slowed progression or if patient may be in partial remission. Another three-month period is to verify that kidney disease has stopped progressing at a measurable rate.

If results confirm disease progression has stopped or slowed dramatically, patient can choose to stay on the diet to try for further gains or move to the maintenance diet. Maintenance diet is designed to keep the gains made during the prior year; but be much easier to manage and allow more food choices. Maintenance diet will be lifelong for most patients, but their disease progression may be slowed dramatically. If diet is changed back to a diet that contributes to oxidative stress, acidosis and inflammation disease progression may continue. In addition, protein nutrition will be poor.

METHODS OF TREATMENT

Disclosed herein are methods of treatment of the diseases, disorders, and conditions listed in Table 6, and using the steps illustrated in Table 7.

It also comprises determining which formulation of Tables 1-4 to administer. This is based largely on the patient's type and severity of their medical condition. The range of formulas allows patients and doctors to do four things: 1. Provide protein nutrition 2. Control magnesium intake and serum magnesium levels 3. Control calcium intake and serum calcium levels 4. Specific nutrition for each stage of kidney disease to reduce the risk of heart disease and vascular calcification.

The composition is in a tablet form, each tablet comprising: 1) 100% magnesium salts of the keto-acids; or 2) both magnesium and calcium salts for each keto-acid.

TABLE 7 of Diseases, Disorders, and Conditions Treatable via the Administration of Compositions Kidney disease including dialysis
Liver disease
Age related kidney decline
Pre-surgery to improve recovery times and decrease risk
if albumin levels are below 4.6
Post-surgery to improve recovery times and decrease risk
if albumin levels are below 4.6
Pre-hospitalization/pre-operative to decrease
morbidity/morality rates and decrease
risk to patient if albumin levels are below 4.6
Post hospitalization/Post-operative to decrease

TABLE 7-continued of Diseases, Disorders, and Conditions Treatable via the Administration of Compositions morbidity/mortality rates and decrease risks
to patient if albumin levels are below 4.6
Cancer/Chemotherapy patients with impaired metabolism
and albumin level below 46
Protein energy wasting (PEW)
Sarcopenia
Age related decline in muscle mass if albumin
levels are below 4.6
Reduce recovery time for professional athletes who train
or compete daily/frequently
Acute and or chronic inflammation
Malnutrition and or protein malnutrition if albumin
levels are below 4.6
Crohn's disease if albumin levels are below 4.6
Burn patients if albumin levels are below 4.6
Sepsis if albumin levels are below 4.6
Heart failure if albumin levels are below 4.6
Ischemic Stroke if albumin levels are below 4.6
Transplant recipients if albumin levels are below 4.6

Table 8 discloses the general steps with exemplified computations in an embodiment of computing the proper baseline dose for a patient to take of any one of the compositions of Tables 1-4. In step 1, the patient's body weight in kilograms is multiplied by 0.8 to determine their total daily protein requirement. In step 2, determine the current protein intake or proposed protein intake based on low or very low protein diet. In step 3, subtract dietary protein requirement from dietary protein restriction. In step 4, determine current protein intake, or proposed protein intake, based on a low or very low protein diet; and then solve for supplement protein requirement using body weight using shortfall. In step 5, use an estimate of one pill equals 4 grams of dietary protein to solve to correct dosage for equivalent of 60 grams of protein per day.

This is the first step in calculating correct dosage. This approach allows the lowest amount of nitrogen and ammonia workload on the kidneys for the first ninety days. At this stage, Blood urea nitrogen levels and creatinine levels are higher than normal or outside the normal range. The smallest dose possible is used for the first ninety days to give the kidneys a chance to work off the excess ammonia and nitrogen waste products. Dosage will be corrected every 90 days going forward.

TABLE 8

| Step | Exemplary Computation-Baseline dose |
|---|---|
| 1 | 75 kg patient weight * .8 = 60 kgs of dietary protein |
| 2 | .4 kg for dietary protein restriction * 75 kg weight = 30 grams/day from dietary protein |
| 3 | .8-.4 = .4 grams per kg |
| 4 | 75 kg *.4 = 30 grams; 30 grams/4 gram per pills = 7.5 pills per day |
| 5 | 7.5 pills rounded up to 8 pills |
| | Second Dose Computation |
| 6 | Repeat steps 1-5 to ensure base dosage is correct. |
| 7 | 4.5 g/dl – 3.5 g/gl = 1 g/dl shortfall |
| 8 | 1 × 3 = 4 pills so new total is now 8 + 3 = 11 pills per day |

Second dosage computation: After the first ninety days, a serum albumin test should be done to determine if current dosage is sufficient to raise albumin levels and provide adequate protein nutrition. Using these test results the following calculation should be used to determine new dosage. In Table 8, step 6, repeat steps 1-5 to ensure base dosage is correct in case of body weight changes or dietary changes. If a lower or higher protein diet is used, then dosage must be recalculated.

In step 7, the minimum albumin goal is 4.0 g/dl, and the optimal level is 4.5 g/dl or higher. If current albumin dosage is below 4.0 g/dl, use desired levels of 4.5 g/dl minus current albumin level to determine shortfall amount (as exemplified in Table 7). In step 8, the shortfall amount times 4 equals the number of pills that should be added to the baseline or base dosage.

Alternatively, in step 7, if the albumin level is above 4.0 g/dl, but lower than 4.5 g/dl, the patient may stay on the same dosage for the next ninety day cycle, or may use the same formula to adjust dosage.

Sarcopenia and protein energy wasting base dosage: for patients not on a low or very low protein diet, this low nitrogen protein food can be used to increase albumin, but dosage is different. The optimal level of 4.5 g/dl minus current aluminum levels equals shortfall (4.5 g/dl minus 3.5 g/dl). The shortfall amount times 5 equals the number of pills needed, and no base dosage is used (5×1=5 pills per day).

Sarcopenia and protein energy wasting second dosage: continue to correct using same dosage at ninety-day increments. As albumin rises, dosage will automatically lower or increase based on current albumin levels. The formula is self-correcting. Once an albumin level of 4.0 g/dl is achieved, patient may continue on the same dosage, or may adjust again to increase the albumin levels closer to 4.5 g/dl.

Method of Making the Magnesium Salts of the Alpha Keto Acids

Figure 16:
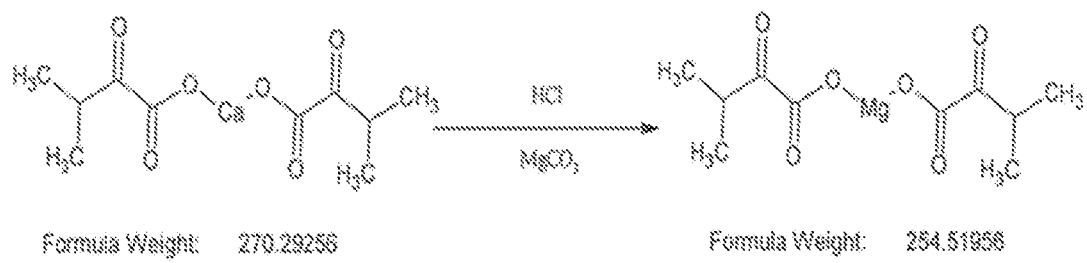
FIG. 16 illustrates the chemical reactions for the manufacturing process of the magnesium salt of the alpha keto acid of valine.

Table 9 discloses the specific method of manufacturing the magnesium salt of the alpha keto acids of: valine (FIG. 14), leucine (FIG. 15), and isoleucine (FIG. 16). In general, the process comprises combining the raw materials of: the calcium salt of the amino acid, water, hydrochloric acid, methyl tert-butyl ether, and magnesium carbonate; stirring the composition for about thirty minutes; allowing to settle into two layers, and collecting the top organic layer to which water and magnesium carbonate are added; heat for about one hour to about 60-65 degrees Celsius; remove solvent, cool, add methyl-tert-butyl ether; stir for about one hour at about 25-30 degrees Celsius; and filter, wash, dry under vacuum, store as powder. Convert powder into an orally consumable "low nitrogen" food product: e.g. food, beverage, tablet, etc.

The manufacturing process disclosed herein does not involve the usage of the following ICH class –1 solvents i.e. Benzene, carbon tetrachloride, 1,2-Dichloroethane and 1,1,1-trichloroethane. And the solvents of class-2 and class-3 used in the manufacturing process are within the acceptance criteria of ICH requirements. And the compounds have tested safe for microbial levels: total microbial count; yeast and mold count; absence of bacterial strains comprising *Escherichia coli*, *Salmonella*, and *Pseudomonas aeruginosa*.

TABLE 9

Method of Making Magnesium Salt of Alpha Keto Acid of Leucine, Isoleucine, and Valine

| Step No. | Leucine Qty. | Isoleucine Qty. | Valine Qty. | Procedure |
|---|---|---|---|---|
| 1. | | | | Check the cleanliness of the reactor |
| 2. | 570.0 ml | 2.39 L | 280.0 ml | Charge water to the reactor |
| 3. | 100.0 gm | 418 ml | 50.0 gm | Charge Keto amino acid calcium salt |
| 4. | 480.0 ml | 2.04 L | 240.0 ml | Charge methyl tert-butyl ether, stir for 15 min |
| 5. | | | | Stir for 5 minutes |
| 6. | 60.0 ml | 0.32 L | 30.0 ml | Add hydrochloric acid to pH-1-2 |
| 7. | | | | Stir for 30 min |
| 8. | | | | Allowed to settle and separate the two layers |
| 9. | | | | Separate the bottom aqueous layer |
| 10. | | | | Collect the top organic layer separately |
| 11. | | | | Transfer the organic layer back to reactor |
| 12. | 300.0 ml | 1.25 L | 150.0 ml | Charge process water in the mass, stir for 15 min |
| 13. | | | | Allowed to settle and separate the two layers |
| 14. | | | | Separate the bottom Aqueous layer |
| 15. | | | | Collect the top organic layer separately |
| 16. | | | | Transfer the organic layer back to reactor |
| 17. | 800.0 ml | 3.34 L | 400.0 ml | Charge water in to the organic layer |
| 18. | 25.2 gm | 84.2 gm | 12.6 gm | Charge magnesium carbonate |
| 19. | | | | Heat to 60-65° C. for 1 hour |
| 20. | | | | After temperature maintains, distill of the solvent completely under vacuum at below 70° C. |
| 21. | | | | Cool the residue to 25-30° C. |
| 22. | 300.0 ml | 1.25 L | 150.0 ml | Add methyl-tert-butyl ether |
| 23. | | | | Stir for 1 hour at 25-30° C. |
| 24. | 200.0 ml | .836 L | 100.0 ml | Filter, wash with methyl tert-butyl ether |
| 25. | | | | Dry the material at 70-75° C. under vacuum till specification meets |
| 26. | 52.0 gm | 180 gm | 32.0 gm | Unload the material in to double polythene bag, store in HDPE containers |

Figure 17:
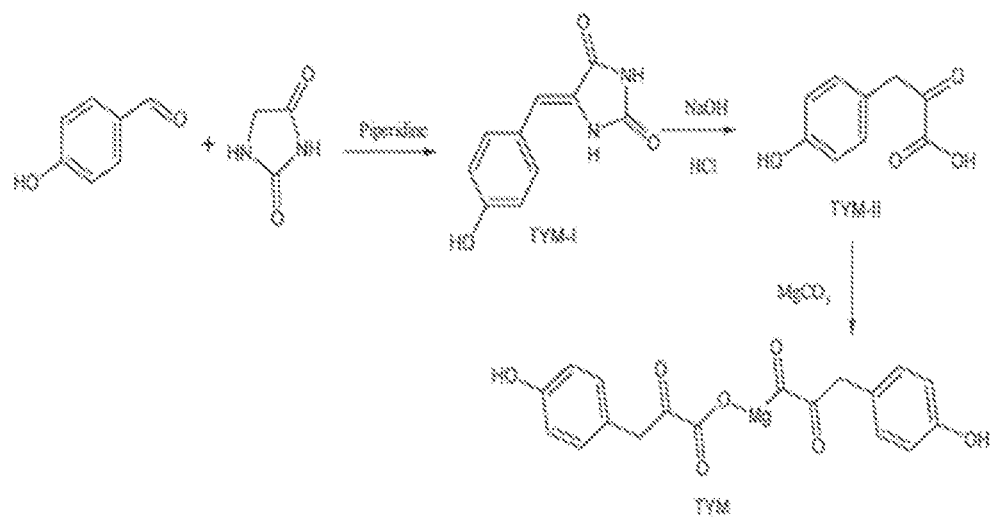
FIG. 17 illustrates the chemical reactions for the manufacturing process of the magnesium salt of the alpha keto acid of tyrosine, which does not comprise nitrogen.

The magnesium salt of the alpha keto acid of tyrosine is produced using the protocol of Appendix A and FIG. 17. It is a three-stage process comprising: the production of 5[4-hydroxyphenyl) methylidene] imidazolidine-2,4-dione (TYM-I) in stage 1 (Table 10); the production of 3-(4-hydroxyphenyl)-2-oxopropanoic acid (TYM-II) in stage 2 (Table 11); and the production of Tyrosine Keto magnesium (TYM) in stage 3 (Table 12).

The tyrosine keto magnesium salt manufactured by the process of FIG. 17 meets the specifications of the heavy metals as per ICH guidelines. And the compounds have tested safe for microbial levels: total microbial count; yeast and mold count; absence of bacterial strains comprising *Escherichia coli*, *Salmonella*, and *Pseudomonas aeruginosa*.

And the tyrosine keto magnesium salt manufactured by the process of Appendix A does not involve the usage of the following ICH class –1 solvents i.e. benzene, carbon tetrachloride, 1,2-Dichloroethane and 1,1,1-trichloroethane. And the following solvents class-2 and class-3 are involved in the manufacturing process of Tyrosine Keto Magnesium salt are within the acceptance criteria of ICH requirements.

Pill Formulation

The formulations in the compositions of the present disclosure may be administered orally in a pill or tablet form to improve patient compliance and control of dosage. It is also noted that they may be formulated into drink and/or food products, such as by way of non-limiting examples comprises: smoothies, shakes, yogurts; nutritional bars and baked goods; sports drinks and supplements; etc.

Traditional medical foods, or amino acid supplements, for kidney patients are powders. Powders are difficult to measure and mix for many patients due to lifestyle and work constraints. For example, essential amino acids powders require a blender in many situations and taste is not pleasant.

A pill containing 775 to 800 mg of essential amino acids—allows patients very precise control. Patient compliance is the holy grail of many treatments and this is no exception. Ease of use and consistency of dosage are key factors in patient compliance and success. Easy to remember dosages are required for long-term management of chronic diseases. Pills size may vary.

Pill Coatings

Pills comprising one each of the compositions of the present disclosure are coated to limit bitter taste and aftertaste. Keto amino acids have a very bitter taste and are very unpleasant. A coated pill, or a film coated pill, using natural ingredients to mask or cover the taste is required. If powders are used, artificial colors and flavorings are used to mask the taste. It takes an incredible amount of these ingredients to effectively mask the taste. Patients prefer and need supplements that do not increase artificial or chemical ingredients. This is especially true for kidney patients who have impaired metabolism of many ingredients. Adding ingredients to mask taste may contain restricted items like sodium, potassium and phosphorus. This version contains no sodium, potassium or phosphorus as a pill where powders may contain these restricted ingredients.

Solid dosage forms for oral administration may include capsules, tablets, caplets, pills, troches, lozenges, powders, and granules. A capsule typically comprises a core material comprising a composition of the invention and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylenevinyl acetate copolymers; and shellac (purified lac). Some such polymers may also function as taste-masking agents.

Tablets, pills, and the like may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to well-known methods in the art.

Suitable fillers for use include, mannitol and other similar agents. Suitable disintegrants include starch derivatives such as sodium starch glycollate. Suitable lubricants include, for example, magnesium stearate.

These solid oral compositions may be prepared by conventional methods of blending, filling, tableting or the like. Repeated blending operations may be used to distribute the active agents throughout those compositions employing large quantities of fillers. Such operations are, of course, conventional in the art.

CONCLUSION

Other features that are considered as characteristic for the various embodiments are set forth in the appended claims.

Although the various embodiments are illustrated and described herein as embodied in nutritional compositions and food products, it is nevertheless not intended to be limited to the details shown, since various modifications and structural changes may be made therein without departing from the spirit of the invention and within the scope and range of equivalents of the claims.

The product names used in this document are for identification purposes only. All trademarks and registered trademarks are the property of their respective owners.

APPENDIX A

Manufacturing Process for Tyrosine Keto Magnesium Salt

Stage-I: 5[(4-hydroxyphenyl)methylidene]imidazolidine-2,4-dione (TYM-I)

| S No. | Raw Materials | M. Wt. | Wt. | UOM | Mole | M.R. | Make |
|---|---|---|---|---|---|---|---|
| 1. | P-hydroxy benzaldehyde | 122.12 | 500 | gm | 4.09 | 1.0 | LR Grade |
| 2. | Hydantoin | 100.08 | 450 | gm | 4.49 | 1.1 | LR Grade |
| 3. | Piperidine | 85.15 | 820 | mL | 9.6 | 2.35 | LR Grade |
| 4. | Process water | — | 16225 | mL | | | In house |
| 5. | Hydrochloric acid | 36.46 | 1600 | gm | 14.04 | 2.86 | LR Grade |

Procedure:

| Step No. | Qty | UOM | Procedure |
|---|---|---|---|
| 1. | | | Check for the cleanliness of the reactor |
| 2. | 450 | g | Charge hydantoin |
| 3. | 500 | g | Charge P-Hydroxy benzaldehyde |
| 4. | 820 | mL | Charge piperidine |
| 5. | | | Heat the mass to 125-130° C. |
| 6. | | | Stir the mass for 45 minutes at 130° C. |
| 7. | | | Check for completion of the reaction |
| 8. | | | After completion of reaction, cool the mass to room temperature |
| 9. | 16000 | mL | Charge process water to the cooled reaction mass |
| 10. | | | Stir for 30 minutes |
| 11. | 1600 | g | Add slowly concentrated hydrochloric acid to the mass at 15-20° C. till pH attains 2-3 |
| 12. | | | Stir the mass for 1 hour at RT |
| 13. | | | Filter the precipitated product |
| 14. | 225 | mL | Wash the product with cold water |
| 15. | 670 | g | Dry the product to constant weight-TYM-1 |

Stage-II: 3-(4-hydroxyphenyl)-2-oxopropanoic acid (TYM-II) Raw materials:

| S No. | Raw Materials | M. Wt. | Wt. | UOM | K. Mole | M.R. | Make |
|---|---|---|---|---|---|---|---|
| 1. | P-Hydroxy benzyl hydantoin | 204.18 | 670 | g | 3.28 | 1.0 | TYM-I |
| 2. | Process water | — | 19000 | mL | — | — | In house |
| 3. | Sodium hydroxide | 40.00 | 3790 | g | 94.75 | 28.88 | LR Grade |
| 4. | Hydrochloric acid | 36.46 | 12000 | g | 105.32 | 32.11 | LR Grade |
| 5. | Ethyl acetate | — | 10050 | mL | — | — | LR Grade |
| 6. | Hexane | — | 10050 | mL | — | — | LR Grade |

Process:

| Step No. | Qty | UOM | Procedure |
|---|---|---|---|
| 1. | | | Check for the cleanliness of the reactor |
| 2. | 19000 | mL | Charge process water to the reactor |
| 3. | 3790 | g | Charge sodium hydroxide flakes |
| 4. | | | Stir for 15 minutes, cool to 20-25° C. |
| 5. | 670 | g | Charge TYM-Stage I at 20-25° C. |
| 6. | | | Stir for 15 minutes |
| 7. | | | Heat the mass to 150-160° C. |
| 8. | | | Stir the mass for 4 hours at 150-160° C. |
| 9. | | | Check for the completion of the reaction |
| 10. | | | After completion reaction, cool the mass to 10-15° C. |
| 11. | 8000 | g | Add slowly hydrochloric acid at below 20° C. till pH attains 8-9 |
| 12. | 3350 | mL | Charge hexane to the reaction mass |
| 13. | | | Stir for 15 minutes |
| 14. | | | Allow to separate the two layers. |
| 15. | | | Separate the product aqueous layer. |
| 16. | | | Collect tile top hexane layer separately |
| 17. | | | Charge back the aqueous layer to the reactor |
| 18. | 3350 | mL | Charge hexane |
| 19. | | | Stir for 15 mInutes |
| 20. | | | Allow to separate the two layers. |
| 21. | | | Separate the product aqueous layer. |
| 22. | | | collect the top hexane layer separately |
| 23. | | | Charge hack aqueous layer to the reactor |
| 24. | 4000 | g | Add hydrochloric acid slowly through addition funnel till pH attains 1-2 at below 20° C. |
| 25. | | | Stir the precipitated product for one hour at 10-20° C. |
| 26. | 5025 | mL | Add ethyl acetate to the acidified reaction mass |
| 27. | | | Stir the precipitated product for one hour at 10-20° C. |
| 28. | | | Separate the bottom aqueous layer |
| 29. | | | Collect the top product organic layer separately |
| 30. | | | Charge back the aqueous layer to the reactor |
| 31. | 5025 | mL | Add ethyl acetate to the aqueous layer |
| 32. | | | Stir for 15 min, allow to separate the two layers |
| 33. | | | Separate the bottom aqueous layer |
| 34. | | | Combine all the organic layers |
| 35. | | | Distill of the solvent completely under vacuum at below 50° C. |
| 36. | 2680 | mL | Add hexane to the residue |
| 37. | | | Stir for 30 min |
| 38. | | | Filter the precipitated product |
| 39. | 670 | mL | Wash with hexane |
| 40. | | | Dry the mass to constant weight at 50-60° C. under vacuum |
| 41. | 335 | g | Yield of TYM-II |

Stage-III: Tyrosine Keto magnesium (TYM)

| S No. | Raw Materials | M. Wt. | Wt. | UOM | K. Mole | M.R. | Make |
|---|---|---|---|---|---|---|---|
| 1. | TYM-II | 180.15 | 335 | g | 0.055 | 1.0 | In house |
| 2. | Methanol | — | 5025 | mL | — | — | Commercial |
| 3. | Process water | — | 3000 | mL | — | — | In house |
| 4. | Magnesium carbonate | 84.31 | 693 | g | 0.027 | 0.50 | Commercial |
| 5. | MTBE | | 1850 | mL | | | |

10

Process:

| Step No. | Qty | UOM | Procedure |
|---|---|---|---|
| 1. | | | Check the cleanliness of the reactor |
| 2. | 335 | g | Charge TYM-II |
| 3. | 5025 | mL | Charge methanol |
| 4. | | | Stir the mass for 15 minutes |
| 5. | 3000 | mL | Charge water |
| 6. | 693 | g | Charge Magnesium Carbonate |
| 7. | | | Heat the mass to 55-60° C. for 1 hour |
| 8. | | | Distilled the solvent completely under vacuum at below 70° C. |
| 9. | 1675 | mL | Charge MTBE to the residue |
| 10. | | | Stir for 30 minutes |
| 11. | 167.5 | mL | Filter the precipitated product |
| 12. | | | Wash the material with MTBE |
| 13. | | | Dry the product to constant weight under vacuumat below 70° C. |
| 14. | 188 | g | Yield of Tyrosine Keto Magnesium |

What is claimed is:

1. A nutritional or therapeutic composition safe for oral consumption, comprising:
   a) at least three alpha keto analogue or acid of an amino acid of, or any combination thereof:
      1) a magnesium salt;
      2) a calcium salt;
      3) a calcium salt and a magnesium salt;
      4) wherein the at least three alpha keto analogue of the amino acid comprises:
         i) a α-leucine;
         ii) a α-valine;
         iii) a α-isoleucine;
         iv) a α-phenylalanine;
         v) a α-methionine or an α-hydroxy methionine;
   b) a L-lysine monoacetate, and a L-threonine;
   c) histidine amino acid, or a magnesium salt, or a calcium salt, or a calcium salt and a magnesium salt, of a keto analogue of a α-histidine;
   d) tryptophan amino acid, or a magnesium salt, or a calcium salt, or a calcium salt and a magnesium salt, of a keto analogue of a α-tryptophan; and
   e) wherein the oral composition comprises: a nitrogen load that does not exceed 3.8%; a calcium load that does not exceed 6.5%; a magnesium load that is at least 2.2%; and a sodium load that does not exceed 0.8%.

2. The nutritional or therapeutic composition of claim 1, further comprising a tyrosine amino acid, or a magnesium salt, or a calcium salt, or a calcium salt and a magnesium salt, of a keto analogue of a α-tyrosine.

3. The nutritional or therapeutic composition of claim 1, further comprising:
   about 8 to 31% wt/wt of the alpha keto analogue of leucine;
   about 5 to 21% wt/wt of the alpha keto analogue of valine;
   about 3 to 16% wt/wt of the alpha keto analogue of isoleucine;
   about 6 to 10% wt/wt of the alpha keto analogue of phenylalanine;
   about 3 to 5 wt/wt of the alpha keto analogue of hydroxy-methionine;
   about 9 to 13% wt/wt of L-lysine monoacetate;
   about 5 to 8% wt/wt of L-threonine;
   about 0 to 0.7% wt/wt of tyrosine or the magnesium salt of the alpha keto analogue of tyrosine; and/or about 0 to 0.4% wt/wt of tryptophan, or the alpha keto analogue of tryptophan; and/or
   about 2 to 4v % wt/wt of histidine amino acid, or a calcium or magnesium salt, or non-salt of the α keto analog of histidine.

4. The nutritional or therapeutic composition of claim 1, formulated as a tablet with an excipient comprising one or more of: microcrystalline cellulose, povidone K-30, crospovidone, and magnesium stearate.

5. The nutritional or therapeutic composition of claim 1, comprising:
   1) the magnesium salt of the keto analogue of α-leucine, α-valine, α-isoleucine-α-phenylalanine, α-methionine;
   2) a free amino acid of histidine, or a calcium or magnesium keto analogue of α-histidine;
   3) a magnesium salt of the alpha keto analogue of tryptophan; or a base acid of tryptophan;
   4) L-lysine monoacetate;
   5) L-threonine; and
   6) wherein said composition is to treat kidney disease.

6. The nutritional or therapeutic composition of claim 1, comprising:
   1) the magnesium salt of the keto analogue of α-leucine, α-valine, α-isoleucine, α-tryptophan;
   2) the calcium salt of the keto analogue of α-phenylalanine, α-methionine;
   3) the free amino acid of histidine, or the calcium salt, or the magnesium salt, of the keto analogue of α-histidine;
   4) L-lysine monoacetate;
   5) L-threonine; and 6) wherein said composition is to treat kidney disease.

7. The nutritional or therapeutic composition of claim 1, comprising:
   1) the calcium salt of the keto analogue of α-leucine, α-valine, α-isoleucine, α-phenylalanine, α-hydroxy methionine;
   2) the magnesium salt of the keto analogue of α-tryptophan, α-leucine, α-valine, or α-isoleucine;
   3) the free amino acid of histidine, or the calcium salt, or the magnesium salt, of the keto analogue of α-histidine;
   4) magnesium salt of the keto analogue of tyrosine, or tyrosine amino acid;
   5) L-lysine monoacetate;
   6) L-threonine; and
   7) wherein said composition is to treat stage 4 kidney disease.

8. The nutritional or therapeutic composition of claim 1, comprising:
   1) the calcium salt of keto analogue of α-leucine, α-valine, α-isoleucine, α-phenylalanine, α-hydroxy methionine;
   2) the magnesium salt of the keto analogue of α-tyrosine, or a tyrosine amino acid;
   3) the free amino acid of histidine, or the calcium salt, or the magnesium salt, of the keto analogue of α-histidine;
   4) the magnesium salt of the keto analogous of tryptophan or tryptophan amino acid;
   5) L-lysine monoacetate;
   6) L-threonine; and
   7) wherein said composition is able to treat stage 5 kidney disease.

\* \* \* \* \*